(12) United States Patent
Hammann et al.

(10) Patent No.: US 11,553,952 B2
(45) Date of Patent: Jan. 17, 2023

(54) SURGICAL INSTRUMENTS AND RELATED METHODS

(71) Applicant: NuVasive, Inc., San Diego, CA (US)

(72) Inventors: Conrad Tyler Hammann, Carlsbad, CA (US); Jonathan Daniel Briend, Del Mar, CA (US)

(73) Assignee: NuVasive, Inc., San Diego, CA (US)

( * ) Notice: Subject to any disclaimer, the term of this patent is extended or adjusted under 35 U.S.C. 154(b) by 213 days.

(21) Appl. No.: 17/137,653

(22) Filed: Dec. 30, 2020

(65) Prior Publication Data

US 2021/0196328 A1 Jul. 1, 2021

Related U.S. Application Data

(60) Provisional application No. 62/955,571, filed on Dec. 31, 2019.

(51) Int. Cl.
| | |
|---|---|
| *A61B 17/68* | (2006.01) |
| *A61B 17/80* | (2006.01) |
| *A61B 17/56* | (2006.01) |
| *A61B 17/00* | (2006.01) |

(52) U.S. Cl.
CPC .. *A61B 17/808* (2013.01); *A61B 2017/00477* (2013.01); *A61B 2017/564* (2013.01)

(58) Field of Classification Search
CPC combination set(s) only.
See application file for complete search history.

(56) References Cited

U.S. PATENT DOCUMENTS

| | | | |
|---|---|---|---|
| 8,328,856 B1 | 12/2012 | Donahoe et al. | |
| 2005/0234455 A1* | 10/2005 | Binder | A61B 17/8042 606/294 |
| 2015/0190241 A1 | 7/2015 | Gowan | |
| 2015/0201975 A1 | 7/2015 | Paul | |
| 2015/0201976 A1 | 7/2015 | Humphreys et al. | |
| 2016/0081818 A1 | 3/2016 | Waugh et al. | |
| 2016/0128737 A1 | 5/2016 | Coric et al. | |
| 2021/0153879 A1 | 5/2021 | Walsh et al. | |
| 2021/0153913 A1 | 5/2021 | Walsh et al. | |
| 2021/0154022 A1 | 5/2021 | Walsh et al. | |

* cited by examiner

*Primary Examiner* — Sameh R Boles
(74) *Attorney, Agent, or Firm* — Hoffman Warnick LLC

(57) ABSTRACT

One aspect of the disclosure relates to a surgical instruments and surgical instrument guides, and associated methods. The surgical instrument may include: an elongated body having a distal end; a housing disposed at least partially within the elongated body and pivotably coupled to the elongated body; and an actuator engaged with a proximal end of the elongated body and operably associated with the housing such that the housing pivots about a pivot point upon actuation of the actuator. In another embodiment, the surgical instrument may include: an elongated body having a segmented distal tip; a guide barrel extending longitudinally within the elongated body, the guide barrel being substantially aligned with a bore within the segmented distal tip, wherein the segmented distal tip is configured to transition between an unexpanded configuration and an expanded configuration.

20 Claims, 28 Drawing Sheets

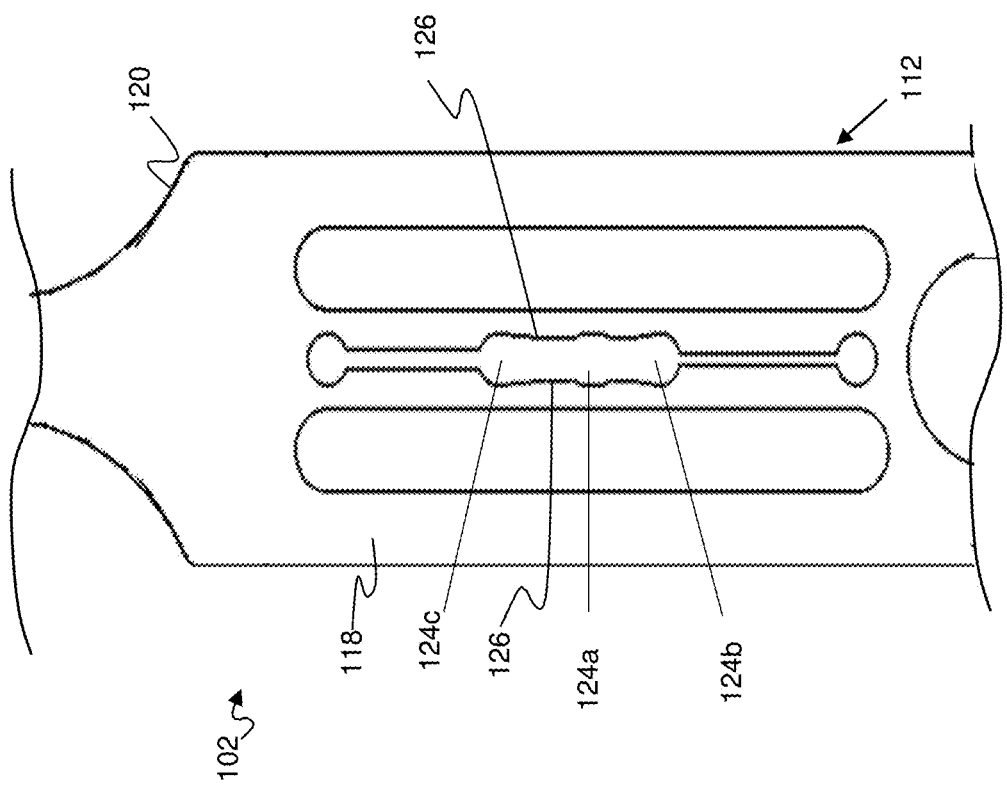

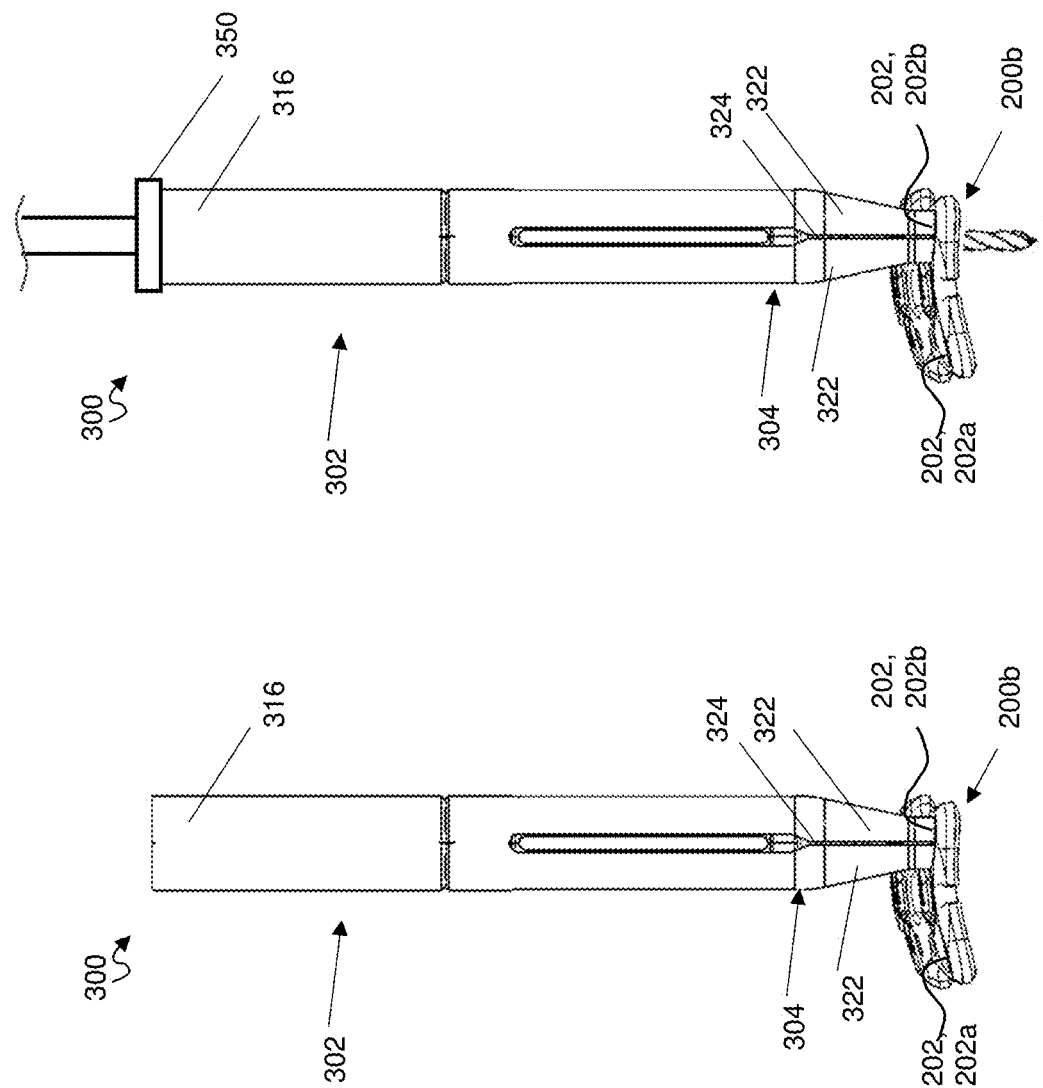

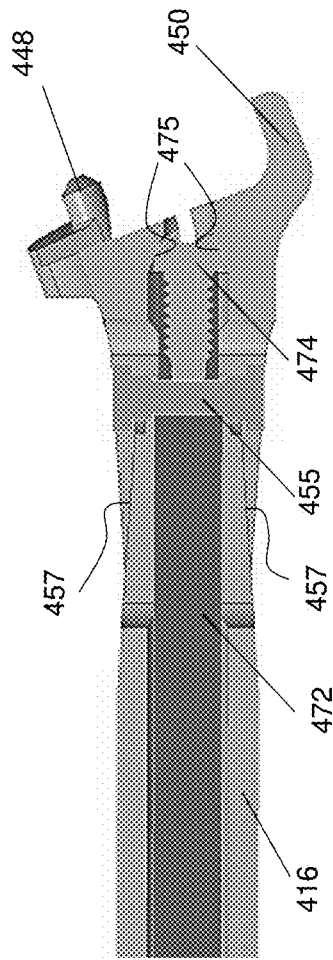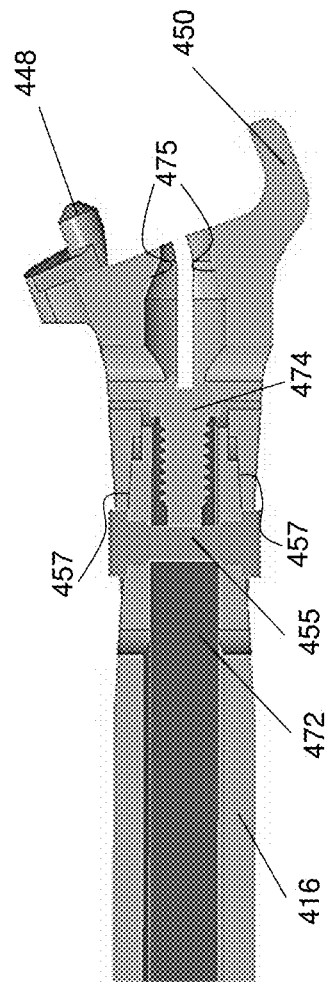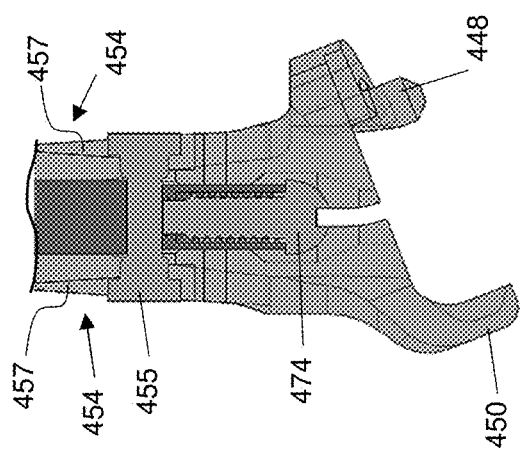
FIG. 35b
FIG. 35c
FIG. 35a

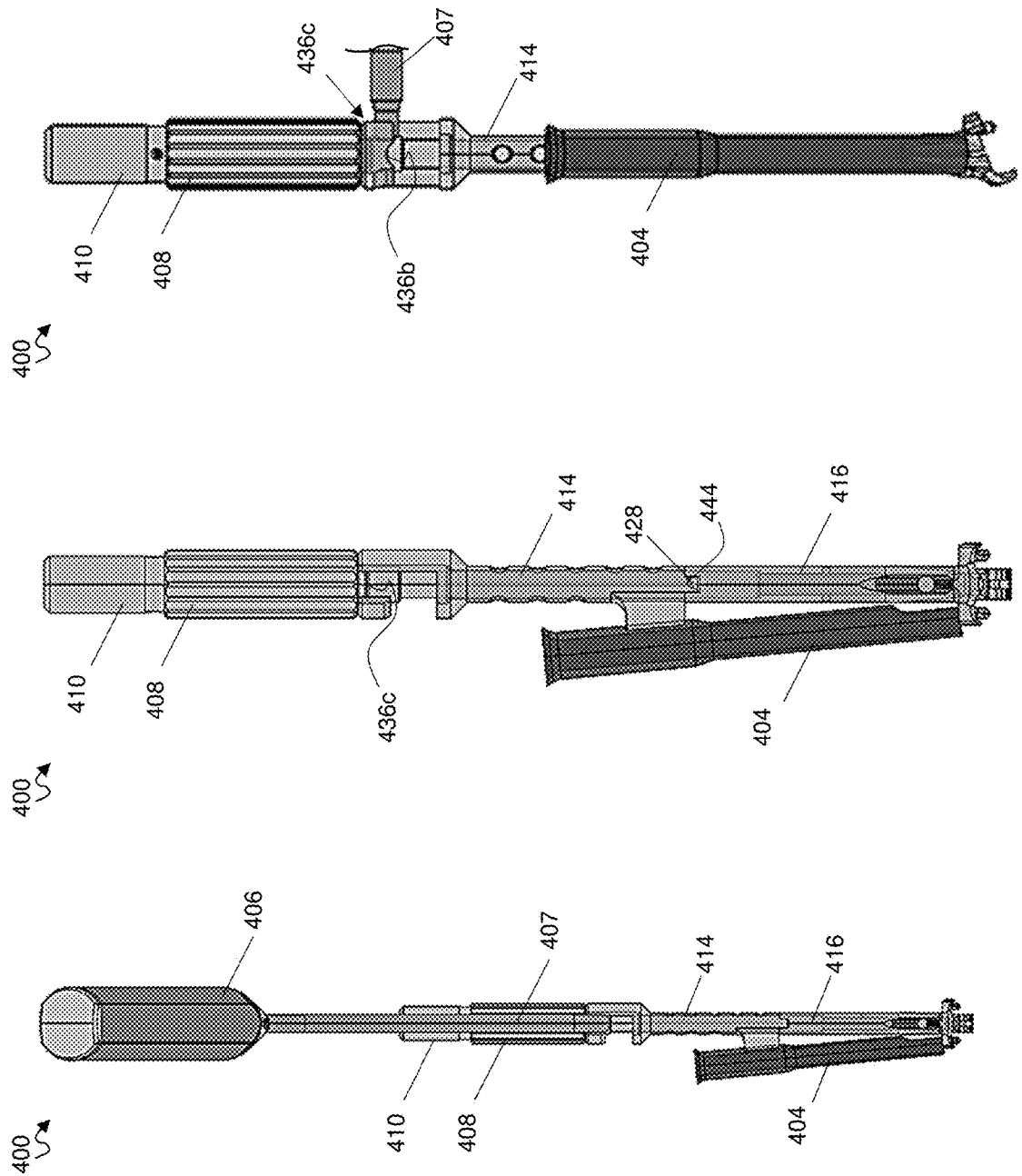

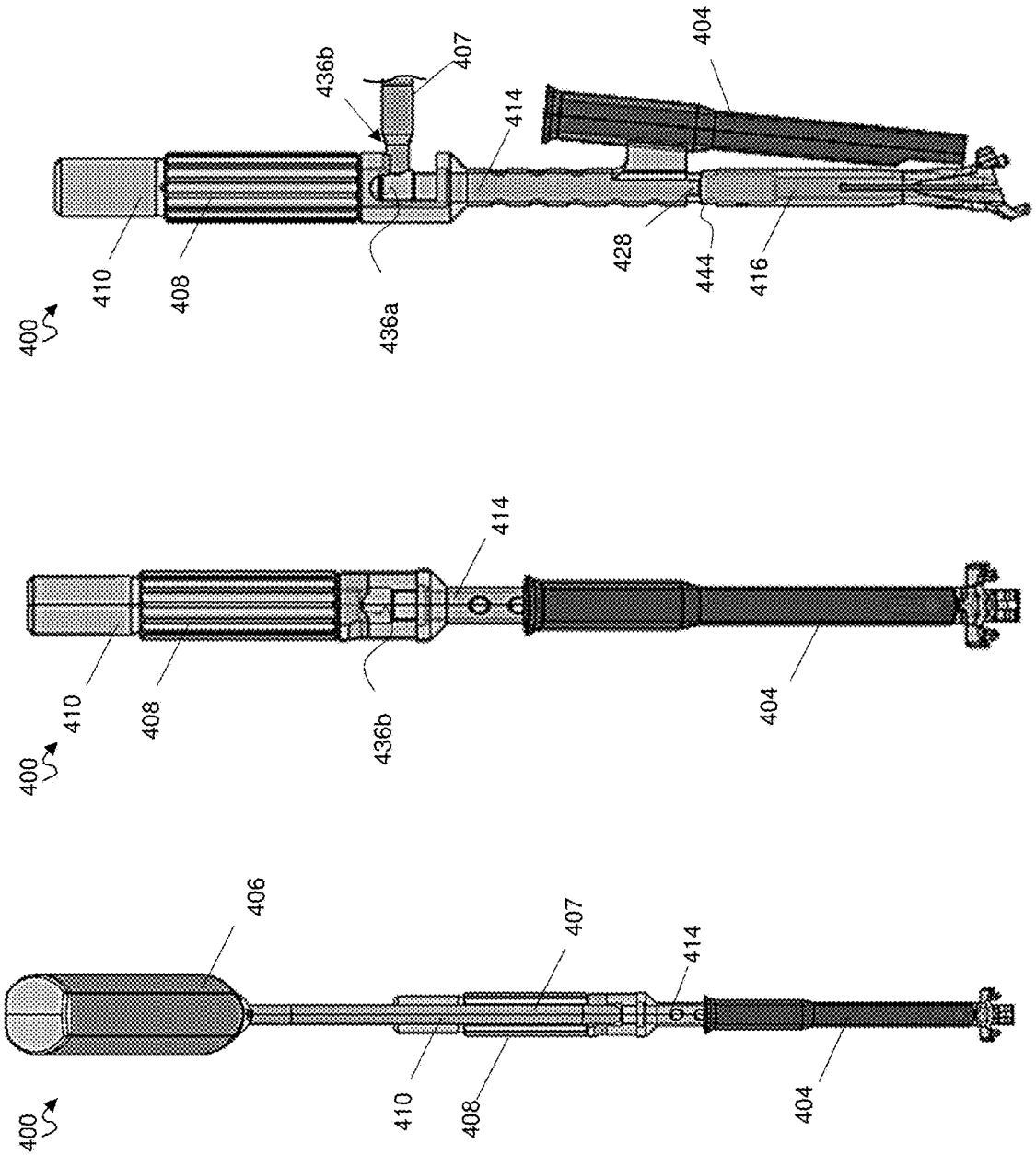

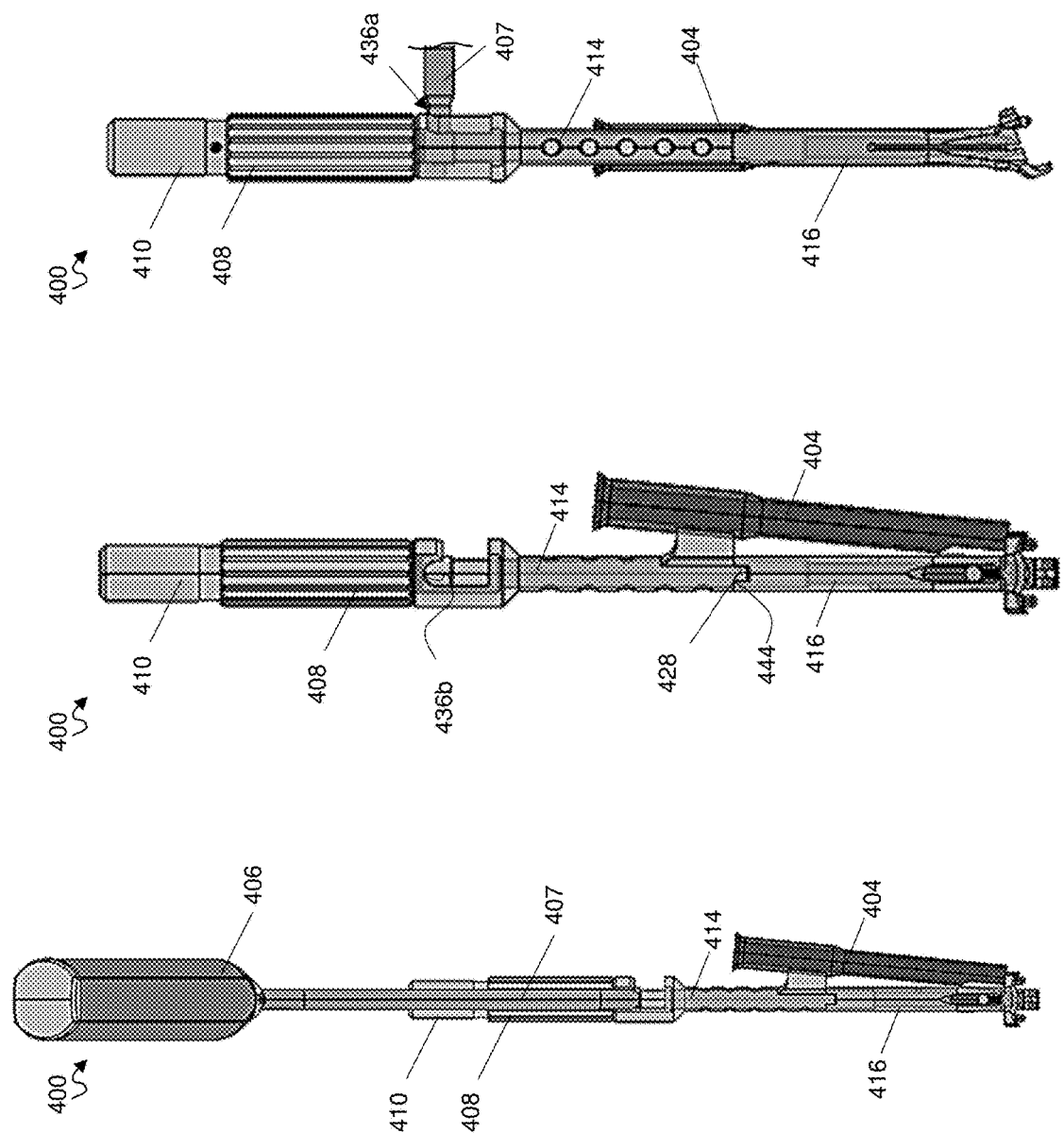

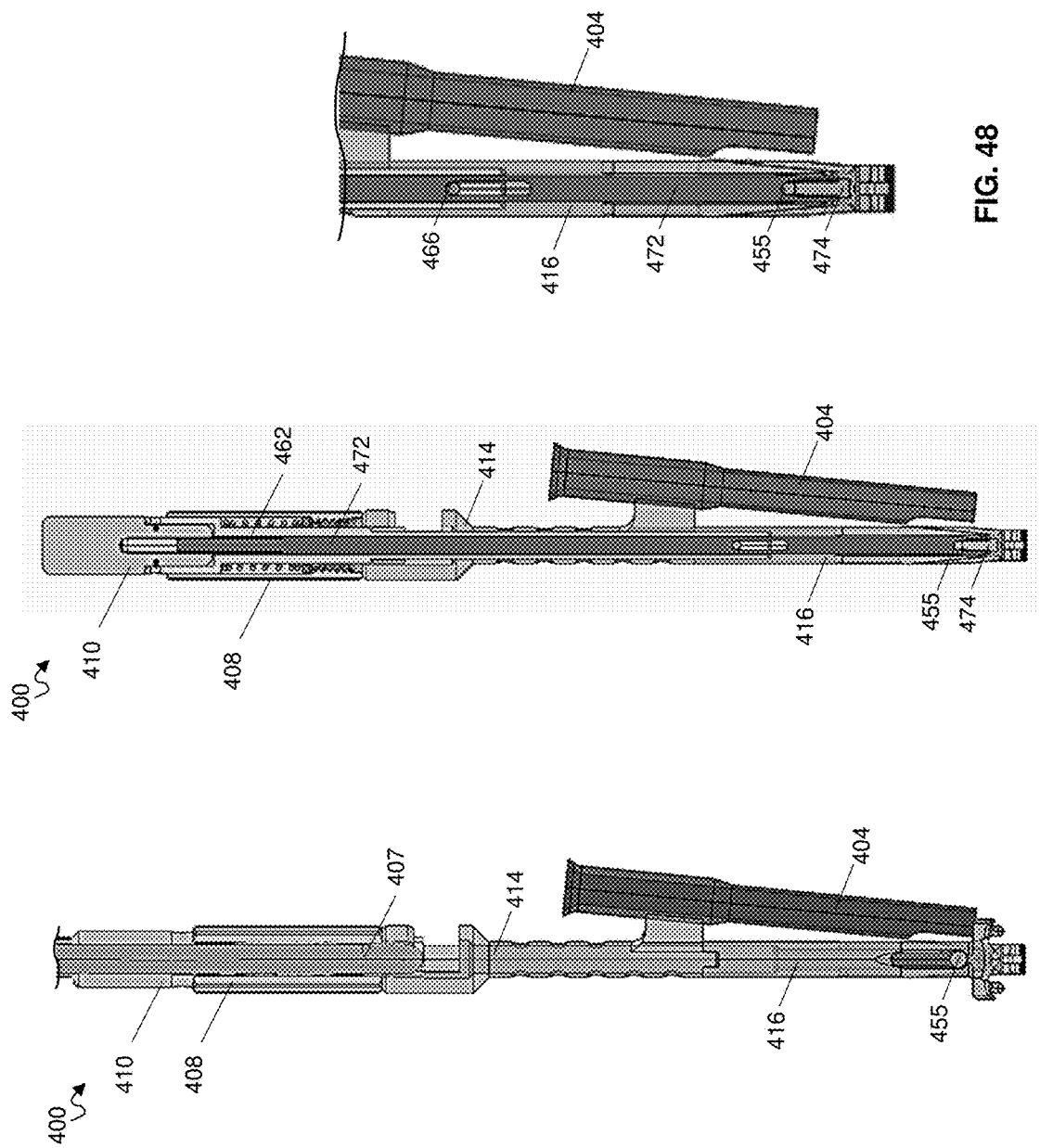

SURGICAL INSTRUMENTS AND RELATED METHODS

TECHNICAL FIELD

The subject matter described herein relates to surgical instrument and surgical instrument guides, and methods associated therewith.

BACKGROUND

Guides are tools that may be used in orthopedic surgeries to assist surgeons with the placement of bone screws or fasteners in attaching surgical bone plates to a bone. A guide is configured to accommodate various tools that may be inserted therein for preparation of the bone for the bone screw. Additionally, Guides aid in the alignment of the tools relative to a desired bone screw trajectory and protect the surrounding anatomy during use of such tools. An example of a procedure which a guide may be used includes an anterior cervical fixation procedure which may follow, for example, a discectomy and/or corpectomy.

During such a procedure, an anterior cervical plate (ACP) is placed alongside vertebral bodies of adjacent cervical vertebrae to provide spinal fixation and stability. ACPs include fixation apertures for the placements of bone screws therethrough such that the ACP is attached to the vertebral body of each of the desired cervical vertebrae. Once the plate is in the desired position, a drill, tap, and screw (DTS) guide may be positioned within or aligned with the fixation aperture in the ACP. Where desired, an awl may be inserted into the barrel of the DTS guide for perforating the anterior cortex of the vertebra. Thereafter, a drill of the desired drill size may be inserted into the barrel of the DTS guide to drill a bore of a desired length into the bone. Subsequently, a tap may be optionally inserted into the DTS guide to thread the bore formed within the bone by the drill. Alternatively, a combination drill and tap tool may be used to form the bore and thread into the bone. Once the bone screw is prepared, the DTS guide is removed and the bone screw is placed via a driver. This process is repeated for each fixation aperture within the ACP until the ACP is appropriately secured.

Conventional DTS guides for anterior cervical procedures typically have a large profile which can interfere with the surgeon's view and/or patient tissue.

SUMMARY

A first aspect of the disclosure relates to a surgical instrument. The surgical instrument may include: an elongated body having a distal end; a housing disposed at least partially within the elongated body and pivotably coupled to the elongated body; and an actuator engaged with a proximal end of the elongated body and operably associated with the housing such that the housing pivots about a pivot point upon actuation of the actuator.

A second aspect of the disclosure relates to a surgical instrument guide. The surgical instrument guide may include: an elongated body having a distal end; a housing disposed at least partially within the elongated body and pivotably coupled to the elongated body; and an actuator engaged with a proximal end of the elongated body and operably associated with the housing such that the housing pivots upon actuation of the actuator, wherein, in a neutral position of the housing, the housing is positioned substantially centered within the elongated body, wherein, in a first use position of the housing, a portion of a proximal end of the housing extends from a first side of the elongated body, and wherein, in a second use position of the housing, a portion of the proximal end of the housing extends from a second, opposing side of the elongated body.

A third aspect of the disclosure relates to a method of inserting bone screws. The method may include: positioning a bone plate having a first fixation aperture and second fixation aperture in a desired position relative to a bone; inserting a guide to a position adjacent the plate at the first and second fixation apertures, actuating the guide to a first use position that allows a first bone screw to be inserted into the first fixation aperture; inserting the first bone screw through the guide into the first fixation aperture; actuating the guide to a second use position that allows a second bone screw to be inserted into the second fixation aperture; and inserting the second bone screw into the second fixation aperture.

A fourth aspect of the disclosure relates to a surgical instrument. The surgical instrument may include an elongated body having a segmented distal tip; a guide barrel extending longitudinally within the elongated body, the guide barrel being substantially aligned with a bore within the segmented distal tip, wherein the segmented distal tip is configured to transition between an unexpanded configuration and an expanded configuration. In some embodiments, the segmented distal tip may include at least one segment. In such an embodiment, the at least one segment may be in an expanded position relative to the elongate body in the expanded configuration of the segmented distal tip and the at least one segment may be in an unexpanded position relative to the elongated body in the unexpanded configuration of the segmented distal tip. In some embodiments, the segmented distal tip may include a plurality of segments. In such an embodiment, each segment of the plurality of segments may be in the expanded position relative to the elongated body in the expanded configuration of the segmented distal tip and each segment of the plurality of segments may be in an unexpanded position relative to the elongated body in the unexpanded configuration of the segmented distal tip.

A fifth aspect of the disclosure relates to a method of inserting bone screws. The method may include: positioning a bone plate having at least a first fixation aperture in a desired position relative to a bone; inserting a guide into the first fixation aperture, wherein the guide includes: an elongated body having a segmented distal tip; and a guide barrel extending longitudinally within the elongated body, the guide barrel being substantially aligned with a bore within the segmented distal tip; and inserting a first bone screw through the guide barrel and through the bore of the segmented distal tip, wherein insertion of the first bone screw includes engaging a head of the first bone screw with segments of the segmented distal tip such that the segments transition from an unexpanded configuration to an expanded configuration. The method may further include fixating the first bone screw within the first fixation aperture and into the bone. The method may also further include removing the segmented distal tip of the guide from the first fixation aperture, wherein the segmented distal tip disengages from the head of the first bone screw thereby returning to the unexpanded configuration upon the removal of the guide from the first fixation aperture.

A sixth aspect of the disclosure relates to a surgical instrument. The surgical instrument includes: an elongate body having a proximal housing and a distal housing, the proximal housing configured to rotate relative to the distal housing and the distal housing configured to engage a bone plate; a barrel fixed to the proximal housing configured to rotate about the elongate body with rotation of the proximal housing; and a first actuator engaged with the proximal housing and operably associated with the proximal housing such that the proximal housing rotates relative to the distal housing upon actuation of the first actuator.

A seventh aspect of the disclosure relates to another surgical instrument. The surgical instrument includes: an elongate body having a proximal housing and a distal housing, the proximal housing configured to rotate relative to the distal housing and the distal housing configured to engage a bone plate; a barrel fixed to the proximal housing configured to rotate about the elongate body with rotation of the proximal housing; and a first actuator positioned proximal to the proximal housing, the first actuator configured to causing locking and unlocking of the distal housing relative to the bone plate.

An eighth aspect of the disclosure relates to another method. The method includes: positioning a bone plate having a first fixation aperture and second fixation aperture in a desired position relative to a bone; positioning a guide adjacent the bone plate at the first and second fixation apertures; locking the guide to the bone plate; positioning the guide to a first use position that allows a first bone screw to be inserted into the first fixation aperture; inserting the first bone screw through the guide into the first fixation aperture; positioning the guide to a second use position that allows a second bone screw to be inserted into the second fixation aperture; and inserting the second bone screw into the second fixation aperture.

BRIEF DESCRIPTION OF DRAWINGS

The accompanying drawings, which are incorporated in and constitute a part of this specification, show certain aspects of the subject matter disclosed herein and, together with the description, help explain some of the principles associated with the disclosed implementations. In the drawings.

FIG. 4 shows an enlarged front plain view of the set of locking features of the elongated body with housing removed therefrom;

FIG. 20 shows a front plain view of the surgical instrument adjacent a bone plate;

FIG. 21 shows a front plain view of the surgical instrument adjacent the bone plate with a tool inserted therein;

FIG. 35a shows an enlarged cross-sectional view of the distal end of the surgical instrument according to the embodiments of FIG. 25;

FIGS. 35b-35c show enlarged cross-sectional views of the of the distal end of the surgical instrument according to the embodiments of FIG. 25 where FIG. 35b is in the unlocked state and 35c is in the locked state;

FIGS. 36-38 show the surgical instrument according to the embodiment of FIG. 25 in a first barrel use position where FIG. 36 shows a front view of the surgical instrument in the first barrel use position, FIG. 37 shows the front view of the surgical instrument with the handle and handle connector removed, and FIG. 38 shows a side the surgical instrument (i.e., rotated 90°) with only a portion of the handle connector showing;

FIGS. 39-41 show the surgical instrument according to the embodiment of FIG. 25 in an insertion position where FIG. 39 shows a front view of the surgical instrument in the insertion position, FIG. 40 shows the front view of the surgical instrument with the handle and handle connector removed, and FIG. 41 shows a side the surgical instrument (i.e., rotated 90°) with only a portion of the handle connector showing;

FIGS. 42-44 show the surgical instrument 400 in a second barrel use position where FIG. 42 shows a front view of the surgical instrument in the second barrel use position, FIG. 43 shows the front view of the surgical instrument with the handle and handle connector removed, and FIG. 43 shows a side the surgical instrument (i.e., rotated 90°) with only a portion of the handle connector showing;

FIGS. 46-48 show the surgical instrument in the unlocked state where FIG. 46 shows a front view of the surgical instrument in the unlocked state, FIG. 47 shows a cross-sectional view of FIG. 46, and FIG. 48 shows an enlarged view of the distal end of the surgical instrument of FIG. 47;

FIG. 49 shows a front view of the surgical instrument in the locked state, FIG. 49 shows a cross-sectional view of FIG. 46, and FIG. 48 shows an enlarged view of the distal end of the surgical instrument of FIG. 49; FIGS. 53 and 55 show an unlocked state and FIG. 54 shows a locked state.

Figure 1:
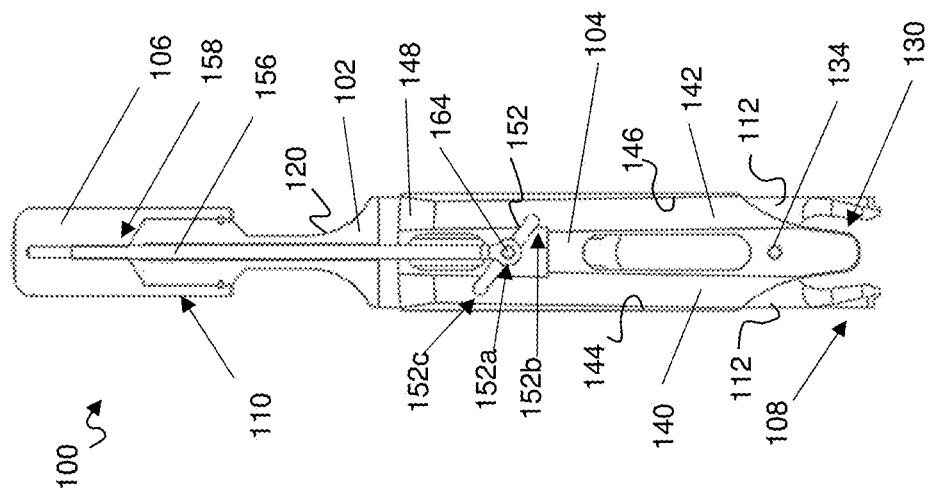
FIG. 1 shows a front plain view of a surgical instrument in a neutral position according to an embodiment of the disclosure.

It is noted that the drawings of the subject matter are not necessarily to scale. The drawings are intended to depict only typical aspects of the subject matter, and therefore, should not be considered as limiting the scope of the disclosed subject matter. In the drawings, like numbering represents like elements between the drawings.

DETAILED DESCRIPTION

The present disclosure describes various embodiments of surgical instruments and surgical instrument guides, and associated methods. For example, the disclosure describes various embodiments of surgical instrument guides and methods associated therewith. In some embodiments, surgical instrument guides of the present disclosure provide for low profile double barrel guides resulting in better visibility for surgeons and less interference with surrounding patient tissue. In some embodiments, surgical instrument guides of the present disclosure have an expandable distal tip to enable passage of larger dimensioned bone screw heads therethrough.

Figure 2:
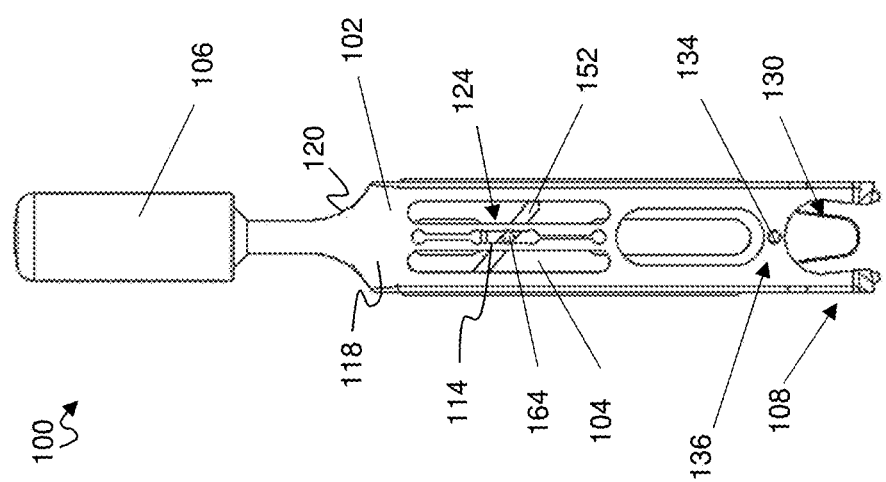
FIG. 2 shows a cross-sectional view of the surgical instrument of FIG. 1.
Figure 3:
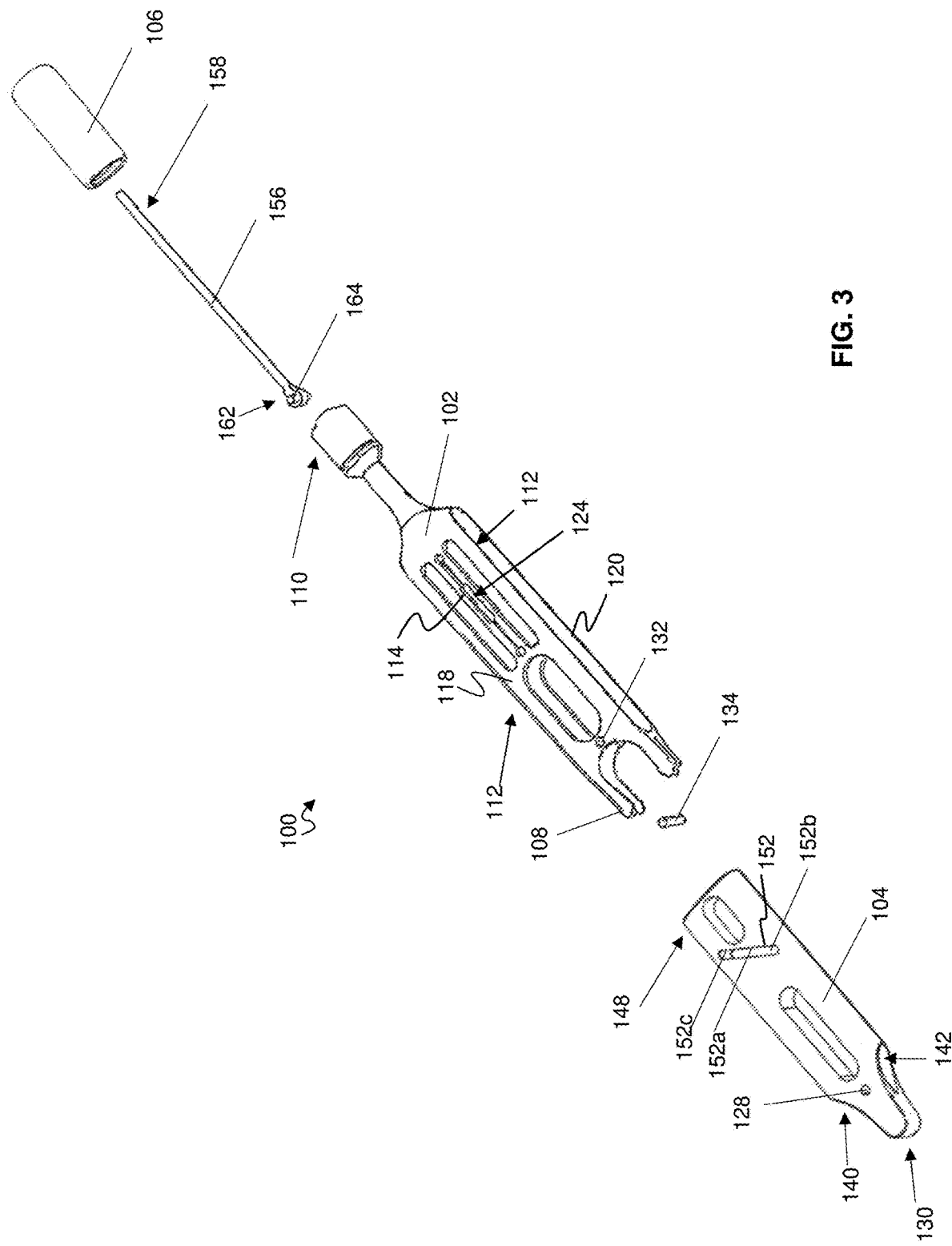
FIG. 3 shows an exploded perspective view of the surgical instrument of FIG. 1.

FIGS. 1 and 2 shows a surgical instrument guide (hereinafter, "guide") 100 in a neutral position. FIG. 3 shows an exploded perspective view of the guide 100. Referring now to FIGS. 1-3 together, a guide 100 according to one embodiment of the disclosure is shown.

The guide 100 includes an elongated body 102, a housing 104, and an actuator 106. As will be described herein, actuation of actuator 106 causes the housing 104 to pivot relative to the elongated body 102.

The elongated body 102 includes a distal end 108 and a proximal end 110 (FIGS. 2-3). The elongated body 102 is sized and shaped to accommodate the housing 104 therein. In some embodiments, the elongated body 102 may be essentially hollow to accommodate the housing 104. The elongated body 102 may include an opening 112 extending longitudinally along at least a portion of each of the opposing sides of the elongated body 102. As will be described herein, the side openings 112 allow for at least a portion of the housing 104 to pass therethrough to enable positioning of the housing 104 in various use positions relative to the elongated body 102.

The elongated body 102 may also include a slot, aperture, slit, passage, and/or opening (hereinafter, "slot") 114 (FIGS. 1 and 3) extending within at least one of a front side 118 (FIGS. 1 and 3) or an opposing back side 120 of the elongated body 102. In some embodiments, both the front side 118 and back side 120 may each include a slot 114 extending therethrough. In such an embodiment, slots 114 within the front side 118 and back side 120 may be identical and substantially aligned with one another. As used herein, "substantially" refers to largely, for the most part, entirely specified or any slight deviation which provides the same technical benefits of the disclosure. The slot 114 of the elongated body 102 may extend along a portion of the elongated body 102 in a direction substantially parallel with the longitudinal axis of the elongated body 102, i.e., extending in a proximal and distal direction relative to the elongated body 102. The slot 114 of the elongated body 102 may include a set of locking features 124. The set of locking features 124 may be disposed about the slot 114 such that the set of locking features 124 extend about the slot 114 in a direction substantially parallel with the longitudinal axis of the elongated body 102. As best shown in FIG. 4, the set of locking features 124 may include a first locking feature 124a, a second locking feature 124b, and a third locking feature 124c. The first locking features 124a may be disposed between second locking feature 124b and third locking feature 124c within slot 114. The set of locking features 124 may be configured as a pair of opposing scalloped portions 126 of the wall adjacent the slot 114. The opposing scalloped portions 126 define areas having a greater slot width and areas having a narrower slot width. Each locking feature 124a, 142b, 124c is defined by the areas having a greater width of the slot 114 and are separated from an adjacent locking feature 124a, 124b, 124c by areas with a narrower width of the slot 114 as defined by the of pair of opposing scalloped portions 126. The set of locking features 124 may also be configured as notches, indentations, and/or cutouts. However, any other configuration or shape of the slot 114 may be used as the set of locking features 124 without departing from the disclosure. As will be described herein, the set of locking features 124 maintains the position of housing 104 relative to elongated body 102 thereby maintaining the housing 104 in various desired distinct positions.

Returning now to FIGS. 1-3, the housing 104 is disposed at least partially within the elongated body 102 and pivotably coupled to the elongated body 102. In such an embodiment, the housing 104 is at least partially surrounded by and/or contained within the elongated body 102. In some embodiments, the housing 104 is entirely contained within the elongated body 102 such that the housing 104 does not add to the overall profile of the elongated body 102 and thereby does not add to the overall profile of the guide 100. In some embodiments, the housing 104 may include an opening 128 (FIG. 3) proximate a distal end 130 thereof while the elongated body 102 may include a corresponding opening 132 (FIG. 3) proximate a distal end 108 thereof. Openings 128 and 132 are configured to be aligned with each other when the housing 104 is disposed within and coupled to the elongated body 102 such that a coupler 134 (FIGS. 1-3) may be disposed within both openings 128, 132. As best show in FIG. 3, according to an exemplary embodiment, the coupler 134 may be a pin. The housing 104 may be pivotably coupled to the elongated body 102 via the coupler 134 within openings 128, 132 such that housing 104 can pivot about the coupler 134 relative to the elongated body 102. In this way, coupler 134 and openings 128, 132 together define a pivot point 136 (FIG. 1). The coupler 134 may be configured as a pin, tab, protuberance, protrusion, prominence, or any other similar features for pivotably coupling the housing 104 and the elongated body 102. However, any other similar feature known in the art may be provided as the coupler 134 without departing from aspects of the disclosure.

According to one embodiment, the housing 104 includes at least two barrels 140, 142 (FIGS. 2-3). The barrels 140, 142 each have a lumen 144, 146 (FIG. 2) that extends through the longitudinal length of housing 104. Each barrel 140, 142 has a proximal opening 148 (FIGS. 2-3) and a distal opening 130 to accommodate insertion of at least a portion of a tool, e.g., a drill, tap, awl, or driver, (not shown) and/or bone screws (not shown) therethrough as will be described herein. Each barrel 140, 142 may also be sized and shaped to allow for rotation of the tool within each barrel 140, 142. The barrels 140, 142 may be positioned substantially parallel to one another and spaced apart from each other within the housing 104.

The housing 104 may also include a slot, aperture, slit, passage, and/or opening (hereinafter, "slot") 152 disposed within at least a portion of housing 104. However, any other similar feature known in the art can be provided as a slot 152 without departing from aspects of the disclosure. In some embodiments, slot 152 may be substantially angled or slanted relative to the longitudinal axis of the housing 104. As such, the slot 152 may include a center point 152*a* (FIGS. 2-3), a lower end 152*b* (FIGS. 2-3) and an upper end 152*c* (FIGS. 2-3). The center point 152*a* may be substantially centered about the slot 152 and disposed between lower end 152*b* and upper end 152*c*. The slot 114 of the elongated body 102 may at least partially overlap slot 152 of housing 104 when the housing 104 is disposed within and coupled to the elongated body 102. As will be described herein, the cooperation of the slots 114, 152 enable and/or control the housing 104 to be positioned in desired positions relative to the elongated body 102.

According to an exemplary embodiment, the actuator 106 engages with proximal end 110 (FIG. 2-3) of the elongated body 102 and is operably associated with the housing 104 such that the housing 104 pivots about a pivot point 136 (FIG. 1) relative to the elongated body 102 upon actuation of the actuator 106. More specifically, the housing 104 may pivot about a coupler 134 relative to the elongated body 102 upon actuation of the actuator 106. The guide 100 may further include a drawbar 156 (FIGS. 2-3) extending longitudinally within at least a portion of each of the actuator 106 and the housing 104. Further, the drawbar 156 may extend at least partially through the elongated body 102. The drawbar 156 may be configured to operably couple the actuator 106 to the housing 104. A proximal end 158 of the drawbar 156 may be threadedly connected to the actuator 106 and a distal end 162 of drawbar 156 may include a coupler 164. The drawbar 156 may be configured as a rod, shaft, coupling device or any other similar feature for operably coupling the housing 104 to the actuator 106. The coupler 164 may be configured as a pin, tab, protuberance, protrusion, prominence, or any other similar feature for operably coupling housing 104 and drawbar 156. However, any other similar features known in the art may be provided as a drawbar 156 and a coupler 164 without departing from aspects of the disclosure.

The actuator 106 is configured to control movement of the drawbar 156 such that, upon actuation of the actuator 106, movement of the drawbar 156 causes housing 104 to pivot about pivot point 136 (FIG. 1). More specifically, the actuator 106 is configured to control movement of the drawbar 156 (thereby controlling position of coupler 164 which is disposed at a distal end thereof) such that the coupler 164 moves in a direction that is substantially parallel to the longitudinal axis of the elongated body 102 upon actuation of the actuator 106. Upon such actuation, the drawbar 156 may slide within each of housing 104 and elongated body 102 such that the drawbar 156 linearly translates relative to the housing 104 and the elongated body 102. The coupler 164 may be configured to be slidingly disposed within both slots 114, 152. Therefore, linear translation of the coupler 164 (due to linear translation of the drawbar 156) causes pivoting or tilting of the housing 104 as the coupler 164 slides within the slots 114, 152 due to the slot 152 of the housing 104 being angled relative to the slot 114 of the elongated body 102.

In some embodiments, the actuator 106 may be a thumbwheel such that upon rotation of the thumbwheel, the drawbar 156 moves in a proximal or distal direction depending the direction of thumbwheel rotation, and thereby causes the coupler 164 to also move in a proximal or distal direction consistent with movement of the drawbar 156. However, any type of actuator capable of adjusting the position of the coupler 164 within slots 114, 152 may be used without departing from aspects of the disclosure such as, but not limited to, a roller, knob, knurl or any other similar feature. In some embodiments, the elongated body 102, the housing 104 and the actuator 106 may be composed of suitable materials known to those skilled in the art and include metal, such as stainless steel and titanium, and plastics. Further, the elongated body 102 and the housing 104 may include various openings or cut outs (not individually labeled) to reduce the amount of material used in manufacturing guide 100.

Figure 5:
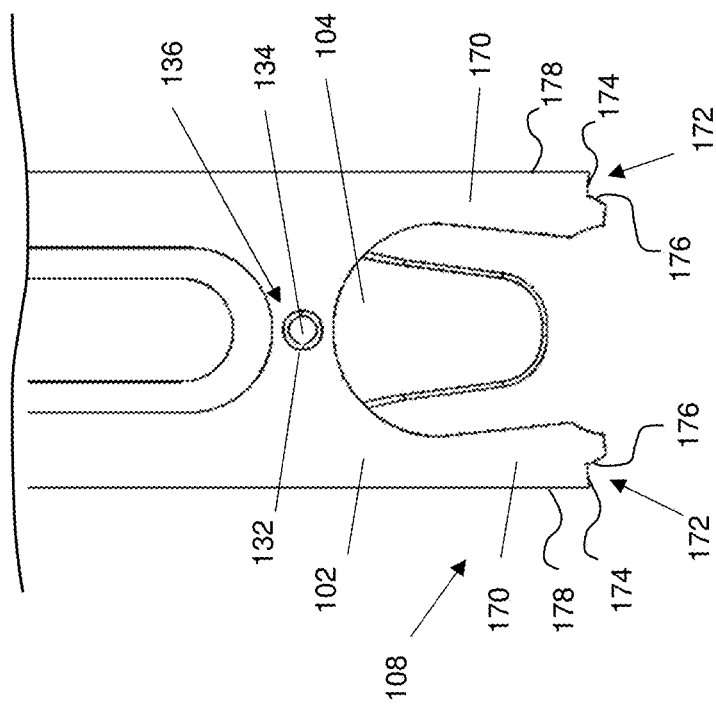
FIG. 5 shows an enlarged front plain view of the distal end of the elongated body of FIG. 1.

Turning now to FIG. 5, an enlarged front plain view of the distal end 108 of the elongated body 102 is shown. As shown, opposing sides of the distal end 108 may each include an extension 170. Each extension 170 may include a step 172. The step 172 facilitates engagement of the guide 100 with a bone plate (not shown) as will be described herein. The step 172 may include a first surface 174 and a second surface 176 substantially perpendicular to first surface 174. The first surface 174 may extend inwardly from an outer side surface 178 of the extension 170 and may be configured to engage an anterior surface of the bone plate. The second surface 176 may extend longitudinally from first surface 174 and may be configured to be at least partially disposed within a fixation aperture within the bone plate when the guide 100 is engaged with the bone plate. As shown in FIG. 5, extensions 170 having steps 172 may be formed on opposing sides of the distal end 108 of the elongated body 102. As will be described herein, this enables each extension 170 to engage with adjacent fixation apertures in a pair of fixation apertures of the bone plate.

Figure 6:
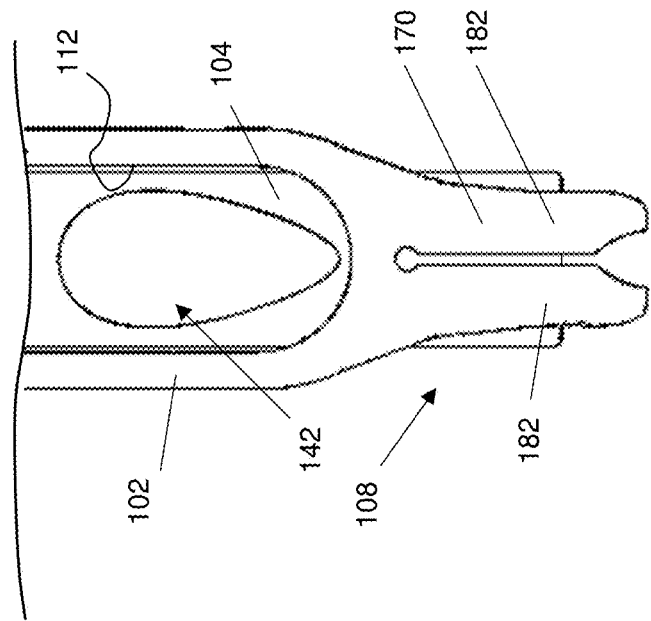
FIG. 6 shows an enlarged side plain view of the distal end of the elongated body of FIG. 1.

FIG. 6 shows an enlarged side plain view of the distal end 108 of the elongated body 102. As shown, the distal end 108 of the elongated body 102 may be segmented. More specifically, the extensions 170 may include at least one segment 182. As will be described herein, the segments 182 may be resilient such that the segments 182 are capable of being displaced and/or expanded when engaged with a head of a bone screw when the bone screw is being inserted into the fixation aperture of the bone plate that the extension 170 is adjacent to or at least partially disposed within.

Figure 11:
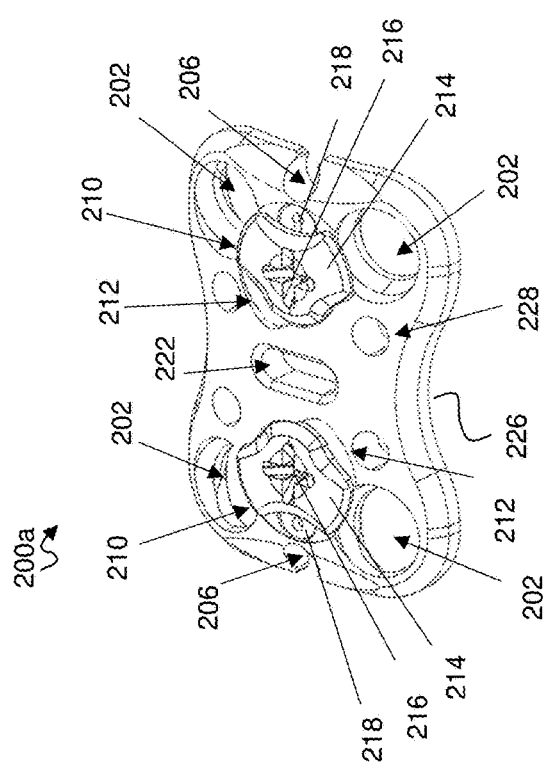
FIG. 11 shows a perspective view of a single-level bone plate according to aspects of the disclosure.
Figure 12:
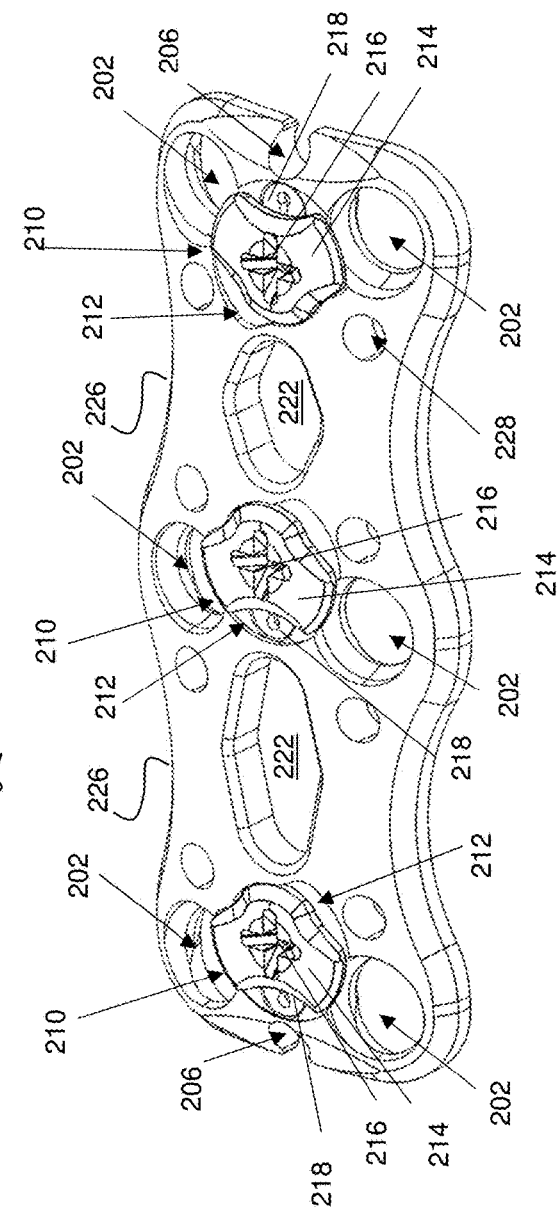
FIG. 12 shows a perspective view of a 2-level bone plate according to aspects of the disclosure.
Figure 13:
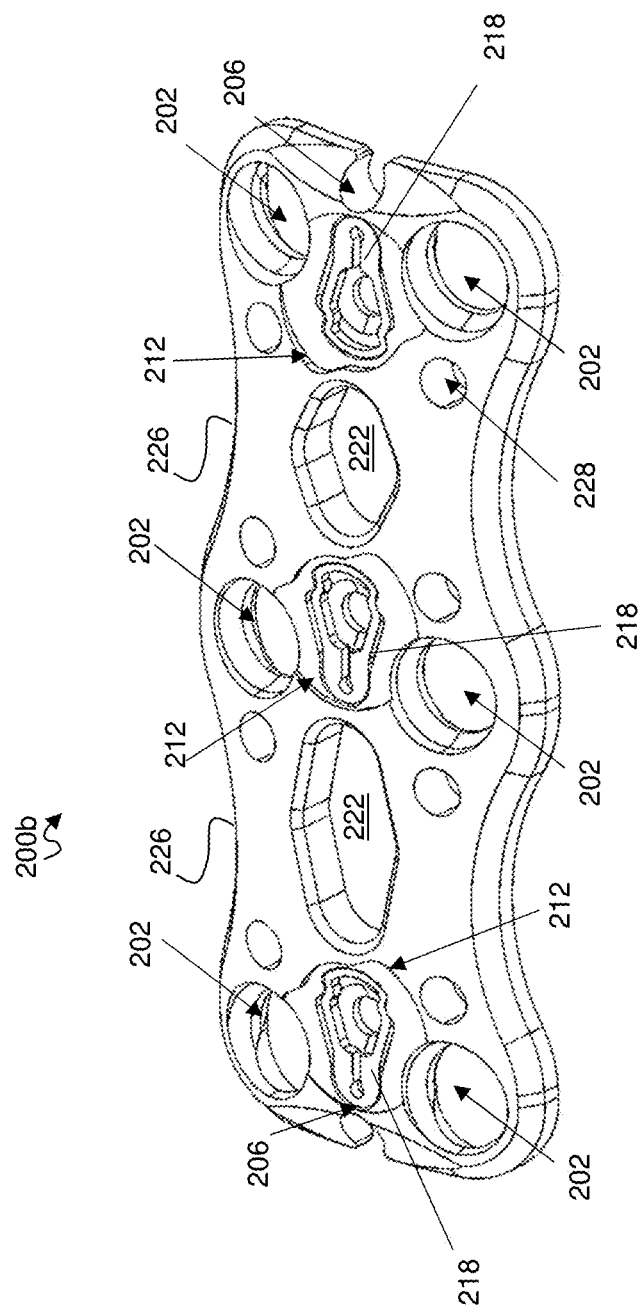
FIG. 13 shows the perspective view of the bone plate according to FIG. 12 with the anti-backout mechanisms removed.

In an alternative embodiment, the distal end 108 of the elongated body 102 may include pins 183 for engaging with and/or docking within pin holes of a plate, e.g., insertion holes 228 (FIGS. 11-13). Surface 174 extends inwardly from an outer side surface 178 of the extension 170 and may be configured to engage an anterior surface of the bone plate In this embodiment, the distal end 108 may not include expandable segments 182.

Returning now to FIG. 1, in a neutral position, the housing 104 is positioned substantially centered within the elongated body 102. In such a position, the housing 104 may be entirely maintained within the elongated body 102. Therefore, the entire profile of guide 100 in this position is only as wide as the width of the elongated body 102. The low profile of the guide 100 due to the housing 104 being entirely maintained within elongated body 102 results in less interference with surrounding patient tissue and better visualization for the user during use compared to conventional guides.

In the neutral position, the coupler 164 is shown as being disposed within both the slot 114 in the elongated body 102 and the slot 152 of housing 104. In this position, the coupler 164 may be positioned within first locking feature 124a of set of locking features 124. First locking feature 124a may be substantially centered relative to slot 114. Additionally, the first locking feature 124a is configured to maintain the coupler 164 in a substantially centered position within the slot 152 in the housing 104. That is, the first locking feature 124a maintains the coupler 164 at the center point 152a (FIG. 2) of the slot 152. This results in the housing 104 being substantially maintained within the elongated body 102. Further, in the neutral position, the barrels 140, 142 at the proximal end 148 of housing 104 are not exposed through side openings 112 of elongated body 102.

Figure 8:
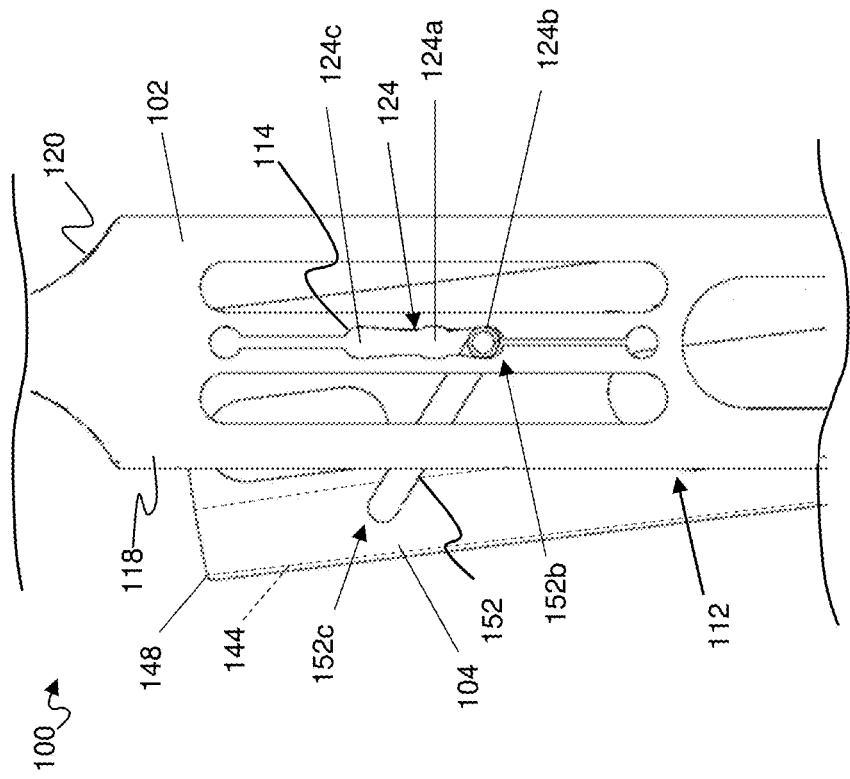
FIG. 8 shows an enlarged front plain view of the set of locking features, the slot of the housing and the coupler of FIG. 7.
Figure 7:
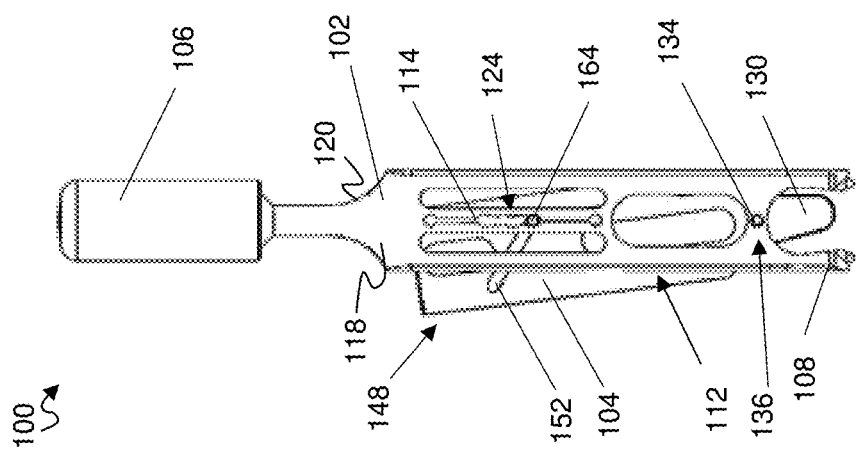
FIG. 7 shows a front plain view of the surgical instrument in a first barrel use position.

Turning now to FIGS. 7-8, a first use position of the housing 104 is shown. In the first use position, a portion of the proximal end 148 of the housing 104 extends from a side of the elongated body 102. More specifically, a portion of the proximal end 148 of the housing 104 is positioned at least partially within the side opening 112 of the elongated body 102 such that the portion of the proximal end 148 of the housing 104 is positioned outside of the elongated body 102. As a result, the first barrel 140 (shown in phantom) is exposed at the proximal end 148 of the housing 104 and is configured to receive a tool (not shown) and/or bone screw (not shown) therein. Further, the opening at the distal end of the first barrel 140 is substantially aligned with the opening at the distal end of the elongated body 102. In this position, the coupler 164 may be positioned within the second locking feature 124b of the set of locking features 124. As shown, the second locking feature 124b is positioned distal to the first locking feature 124a. The second locking feature 124b maintains the coupler 164 in a position within the distal portion of the slot 152 of the housing 104 as compared to a central portion 152a of the slot 152 as when the housing 104 is in the neutral position (as shown in FIGS. 1-2). As discussed herein, the slot 152 in the housing 104 may be angled or slanted relative to the slot 114 in the elongated body 102. Therefore, positioning of the coupler 164 within second locking feature 124b results in the coupler 164 being positioned in the distal, angled end 152b of the slot 152 that corresponds to the second locking feature 124b of the slot 114 in the elongated body 102.

Figure 10:
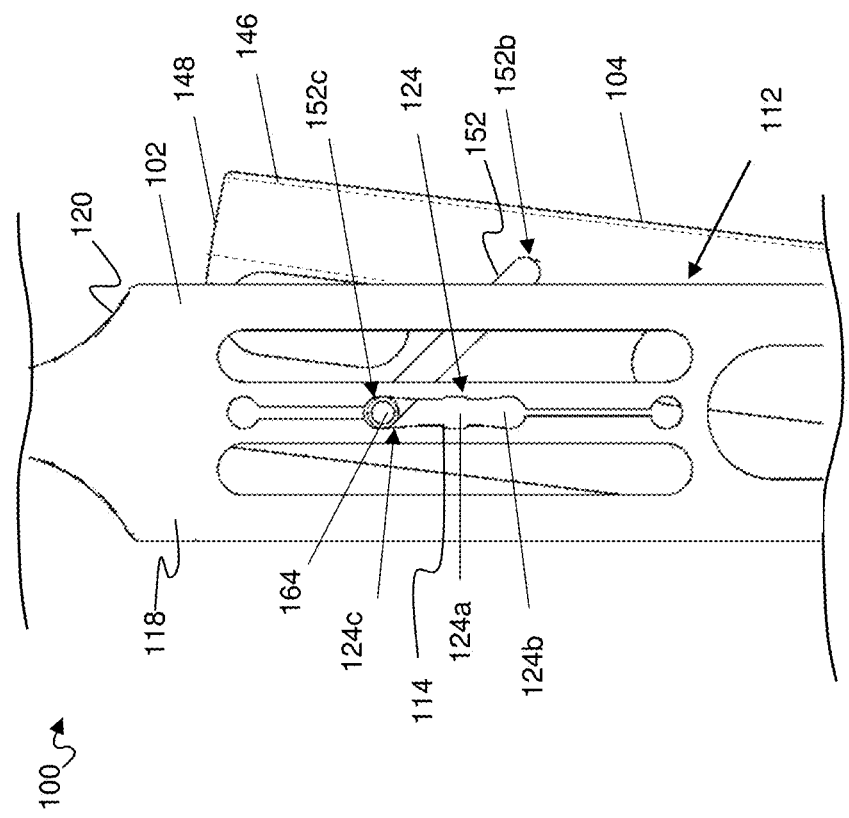
FIG. 10 shows an enlarged front plain view of the set of locking features, the slot of the housing and the coupler of FIG. 9.
Figure 9:
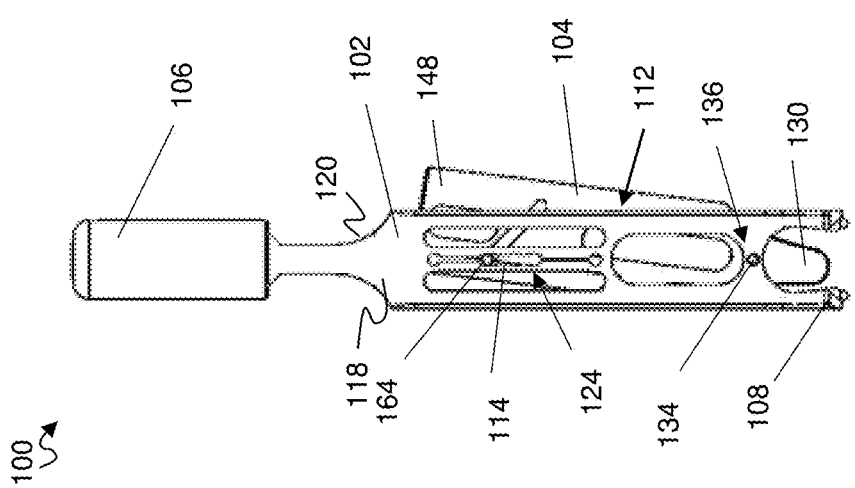
FIG. 9 shows a front plain view of the surgical instrument in a second barrel use position.

Turning now to FIGS. 9-10, a second use position of housing 104 is shown. In the second use position, a portion of the proximal end 148 of the housing 104 extends from a side of the elongated body 102. More specifically, a portion of the proximal end 148 of the housing 104 is positioned at least partially within a side opening 112 of the elongated body 102 such that the portion of the proximal end 148 of the housing 104 is positioned outside of the elongated body 102. As a result, the second barrel 142 (shown in phantom) is exposed at the proximal end 148 of the housing 104 and is configured to receive a tool (not shown) and/or bone screw (not shown) therein. Further, the opening at the distal end of the second barrel 142 is substantially aligned with opening at the distal end of the elongated body 102. In this position, the coupler 164 may be positioned within the third locking feature 124c of the set of locking features 124. As shown, the third locking feature 124c is positioned proximal to the first locking feature 124a. The third locking feature 124c maintains the coupler 164 in a position within the proximal portion 152c of the slot 152 of the housing 104 compared to the central portion 152a of the slot 152 when the housing 104 is in the neutral position as shown in FIGS. 1-2. As discussed herein, the slot 152 in the housing 104 may be angled or slanted relative to the slot 114 in the elongated body 102. Therefore, positioning of the coupler 164 within third locking feature 124c results in the coupler 164 being positioned at a proximal, angled end 152c of the slot 152 in the housing 104 that corresponds to third locking feature 124c of slot 114 in the elongated body 102.

Actuation of the actuator 106 causes the housing 104 to transition between the neutral position (FIGS. 1-2), first use position (FIGS. 7-8) and second use position (FIGS. 9-10). Specifically, actuation of the actuator 106 may cause the drawbar 156 to linearly translate relative to the elongated body 102 and the housing 104. Since the drawbar 156 includes a coupler 164 at a distal end thereof, the coupler 164 also linearly translates relative to the elongated body 102 and the housing 104 upon actuation of the actuator 106. As discussed herein, the coupler 164 is positioned such that the coupler 164 extends within the slot 114 in the elongated body 102 and the slot 152 in the housing 104. Further, the coupler 164 is slidingly disposed within the slots 114, 152 in the elongated body 102 and housing 104, respectively. As a result of linear translation of the coupler 164 (caused by actuation of the actuator 106), the coupler 164 slides within the slots 114, 152 (depending on the direction that the actuator 106 is actuated), and thereby causes the housing 104 to pivot about a pivot point 136. According to the exemplary embodiment, the threaded engagement of the drawbar 156 with the actuator 106 enables the linear translation of the drawbar 156. The drawbar 156 is prevented from rotational movement relative to the elongated body 102 and the housing 104 due to the coupler 164 being disposed within the slots 114, 152.

The set of locking features 124 is configured to maintain the coupler 164, and therefore the housing 104, in distinct desired positions. As discussed herein, each locking feature 124a, 124b, 124c in the set of locking features 124 is configured to maintain the housing 104 in one of the neutral position (FIGS. 1-2), the first use position (FIGS. 7-8) or the second use position (FIGS. 9-10). Due to the scalloped configuration of the set of locking features 124, tactile feedback may be provided to the user as the coupler 164 slides between and engages locking features 124a, 124b, 124c. Further, due to the angled or slanted configuration of the slot 152 in the housing 104 relative to the slot 114 in the elongated body 102, the housing 104 pivots or tilts as the coupler 164 slides within the slot 152, thereby exposing the desired barrel 140, 142 in the first or second use positions.

The guide 100 described herein can be used with a bone plate such as an anterior cervical plate. FIGS. 11-12 show an example of anterior cervical plates according to aspects of the disclosure. FIG. 11 shows a single-level bone plate 200a and FIG. 12 shows a 2-level bone plate 200b. Single-level bone plate 200a allows for fixation of two adjacent vertebrae whereas 2-level bone plate 200b allows for fixation of three adjacent vertebrae. Features of the bone plates 200a, 200b are substantially identical, therefore, like numbering in both FIGS. 11 and 12 represent identical features and bone plates 200a, 200b will not be discussed individually.

The bone plate 200a, 200b includes a set of fixation apertures 202. The fixation apertures 202 enable the bone plate 200a, 200b to be fixed to vertebrae by insertion of bone screws or fasteners (not shown), such as, for example, fixed or variable bone screws therein. The fixation apertures 202 are arranged in pairs of transversely aligned apertures. The number of pairs of fixation apertures 202 may be dependent on the number of levels of desired spinal stabilization. While FIG. 11 shows a single-level bone plate 200a and FIG. 12 shows a 2-level bone plate 200b, a bone plate according to embodiments of the disclosure may also include a 3-level, 4-level, and 5-level bone plate. Each additional level plate will include an additional pair of bone fixation apertures and may or may not include a visualization aperture between sets of additional bone fixation apertures. The bone plate 200a, 200b may optionally include apertures 206 at cranial and caudal ends of bone plate 200a, 200b for temporary tacks or temporary pins (not shown) for temporarily holding bone plate 200a, 200b to bone. Such apertures 206 enable bone plate 200a, 200b, to be temporarily secured to the desired position relative to the desired vertebrae while bone plate 200a, 200b is fixated to the bone (not shown).

The bone plate 200a, 200b may also include an anti-backout mechanism 210 positioned at each pair of fixation apertures 202. Anti-backout mechanisms 210 may be rotatably disposed within recesses 212 formed within the anterior surface of bone plate 200a, 200b. The anti-backout mechanisms 210 may include projections 214 for at least partially covering bone screws that have been inserted into the fixation aperture 202. In this way, anti-backout mechanisms 210 retain bone screws within the fixation apertures 202 once the bone plate 200a, 200b has been fixed to the bone. Anti-backout mechanisms 210 may include a mating feature 216 which can have a shape and/or configuration to allow operable engagement with a complementary feature on a locking instrument (not shown). The locking instrument may engage mating feature 216 of the anti-backout mechanisms 210 and be configured to rotate the anti-backout mechanisms 210 to actuate the anti-backout mechanisms 210 between an unlocked position and a locked position. When anti-backout mechanism 210 is in the unlocked position, the fixation apertures 202 are exposed to allow passage of a bone screw therethrough. After bone screws are inserted into the fixation apertures 202, the anti-backout mechanism 210 can be actuated to the locked position such that projections 214 at least partially cover bone screws within fixation apertures 202 thereby retaining the bone screws within the fixation apertures 202.

Figure 53:
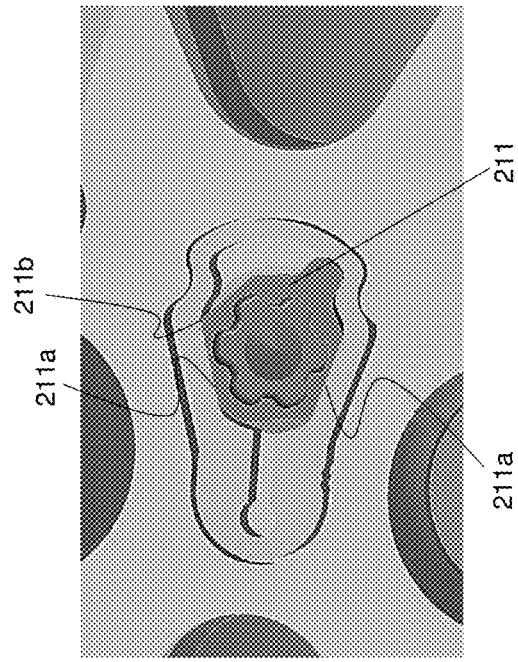
FIGS. 53-55 show an enlarged top view of the engagement of the engagement member of the anti-backout mechanism with the ring member as the anti-backout mechanism is rotated between unlocked and locked states, where
Figure 55:
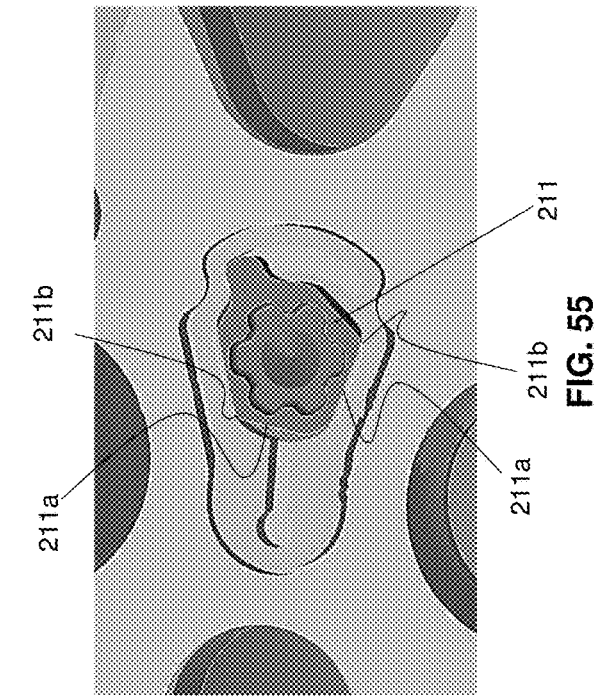
Figure 52:
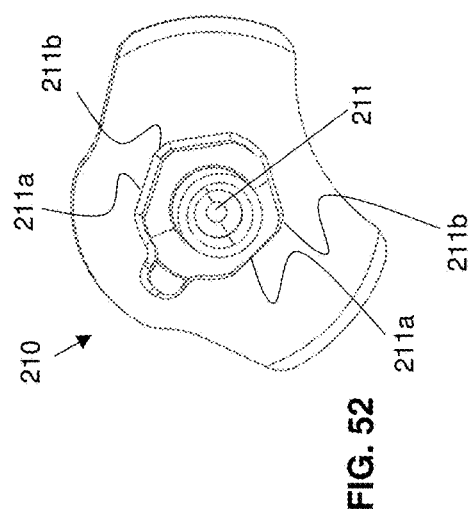
FIG. 52 shows an underside of the anti-backout mechanism according to the embodiment of the bone plate according to FIGS. 11 and 12.
Figure 54:
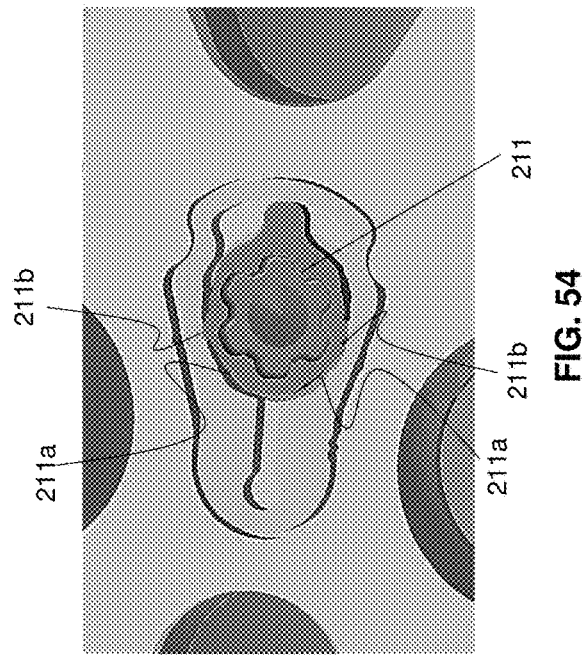

The bone plate 200a, 200b may also include ring or clip member (hereinafter "ring member") 218 positioned within the recesses 212 and beneath the anti-backout mechanisms 210. FIG. 13 shows the bone plate 200b with the anti-backout mechanisms 210 removed so that the ring members 218 can be seen more clearly. The ring members 218 may provide resistance to the anti-backout mechanisms 210 thereby prohibiting the anti-backout mechanisms 218 from rotating after surgery and/or without the locking instrument. Further, the ring members 218 may provide tactile feedback to the user such that the user is able to discern the change in position of the anti-backout mechanism 210 as the anti-backout mechanism 210 transitions between the locked and unlocked position by the locking instrument. Specifically, each ring member 218 may cause an increase in torque as the anti-backout mechanisms 210 transition and/or rotate between the locked and unlocked position. More specifically, the anti-backout mechanisms 210 may include an engagement member 211 (FIG. 52) positioned on an underside of the anti-backout mechanism 210. The engagement member 211 directly interacts with and/or engages the ring members 218 (FIGS. 53-55). As the anti-backout mechanism 210 is rotated relative to the ring member 218, a plurality of flat surfaces 211a and peaks 211b that separate the flat surfaces 211a cause the engagement member 211 to interact with the ring member 218. When the peaks 211b interact with and/or engage the ring member 218, the ring member 218 flexes outward providing a torque delta. As the anti-backout mechanism 210 continues to rotate about the ring member 218, the ring member 218 collapses against the flat surfaces 211a thereby holding the anti-backout mechanism 210 in place.

Bone plates 200a, 200b may be provided having any number of different peripheral profiles, including but not limited to, the generally rectangular peripheral profiles shown in FIGS. 11-12. Bone plates 200a, 200b may optionally include viewing apertures 222 positioned generally within the central portion of bone plate 200a, 200b and between pairs of fixation apertures 202. Viewing apertures 222 provide the ability to see or visualize the spinal target site after the bone plate 200a, 200b has been secured to the patient. It will be appreciated that viewing aperture 222 may be provided in any number of suitable shapes or configurations without departing from the scope of the disclosure, and therefore is not limited to the shape shown by way of example in the Figures.

The bone plate 200a, 200b may also include indentations 226 positioned along the lateral sides of bone plate 200a, 200b between each pair of fixation apertures 202. Optionally, indentations may also be included on cranial and caudal ends of bone plate 200a, 200b. Indentions 226 reduce the amount of material used in manufacturing bone plates 200a, 200b and reduce the overall profile of bone plate 200a, 200b. In addition, the bone plate 200a, 200b may include substantially rounded edges to further reduce the amount of material used in manufacturing and reduce the overall profile. The bone plates 200a, 200b may be of any desired thickness, such as, for example, 1.6 mm, 1.9 mm, or 2.1 mm. However, it is to be understood that other plate thicknesses are also contemplated.

Further, the bone plate 200a, 200b may include a plurality of insertion apertures 228 arranged about bone plate 200a, 200b. Insertion apertures 228 are configured to receive at least a portion of an insertion device (not shown) and may be used to aid the insertion of bone plate 200*a*, 200*b* in a desired position relative to the bone. Insertion apertures 228 may include features complementary to the insertion device to facilitate engagement therewith, such as for example, threads.

Figure 14:
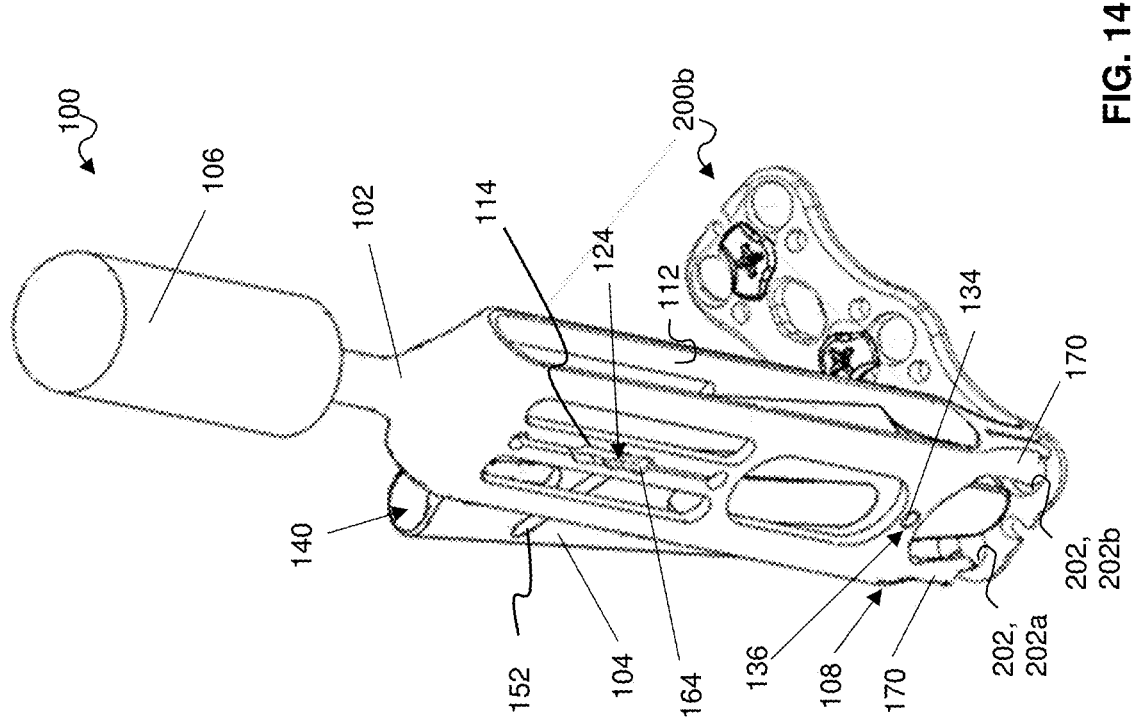
FIG. 14 shows a perspective view of the surgical instrument positioned adjacent the bone plate with a tool inserted therein.

A method of using the surgical instruments described herein may include first positioning an implant requiring fixation to bone in a desired position relative to a bone. According to an exemplary embodiment, the implant requiring fixation to bone is a bone plate. The bone plate may include, for example, the bone plate 200*a* (FIG. 9) or bone plate 200*b* (FIG. 10). FIG. 14 illustrates an exemplary method of use of the guide 100 in conjunction with a bone plate 200*b*. However, it is to be understood that the method is equally applicable to the single level bone plate 200*a*, any conventional bone plate and/or any other implant requiring insertion of instruments or fasteners.

The bone plate 200*b* may include a first fixation aperture 202*a* and a second fixation aperture 202*b*. The guide 100 may be inserted to a position adjacent bone plate 200*b* at the first aperture 202*a* and second fixation aperture 202*b*. Specifically, the guide 100 may be placed adjacent to the bone plate 200*b* such that the distal end 108 of the elongated body 102 is at least partially engaged with the pair of transversely adjacent fixation apertures 202. Each extension 170 of the distal end 108 of the elongated body 102 may engage a respective one of the transversely adjacent fixation apertures 202. More specifically, the first surface 174 (FIG. 5) of the step 172 (FIG. 5) may engage the anterior surface of the bone plate 200*b* and the second surface 176 (FIG. 5) of the step 172 may be at least partially disposed within respective fixation apertures 202 for both extensions 170. During the placement of the guide 100 relative to the bone plate 200*b* in this process, the guide 100 may be positioned in the neutral position such that the housing 104 is maintained within the elongated body 102 and the overall width of the guide 100 is equal to the width of the elongated body 102. As discussed herein, the coupler 164 is positioned in a position at the first locking feature 124*a* of the slot 114 in the elongated body 102 and the center point 152*a* of the slot 152 in the housing 104 while the housing 104 is in the neutral position. Due to the configuration of the first locking feature 124*a* of the slot 114 in the elongated body 102, the coupler 164 is retained therein during the insertion/placement of guide 100 relative to bone plate 200*b*.

Still referring to FIG. 14, the method may also include actuating the guide 100 to a first use position that allows a first bone screw (not shown) to be inserted into first fixation aperture 202*a*. Actuation of the guide 100 to the first use position includes actuating the actuator 106 causing the housing 104 to pivot about a pivot point 136 such that first barrel 140 of housing 104 is accessible to receive the first bone screw to be inserted into first fixation aperture 202*a*. Actuating the actuator 106 causes the drawbar 156 to linearly translate relative to the housing 104 and the elongated body 102. This consequently causes linear translation of coupler 164 which is slidingly disposed within slots 114, 152 in the elongated body 102 and housing 104, respectively. The coupler 164 may slide from a position in the first locking feature 124*a* of the slot 114 in the elongated body 102 and center point 152*a* of the slot 152 in the housing 104 to a position in the second locking feature 124*b* of the slot 114 in the elongated body 102 and the distal portion 152*b* of the slot 152 of the housing 104. As a result of linear translation of the coupler 164 within the slots 114, 152, the housing 104 pivots relative to elongated body 102 about pivot point 136. Pivoting of housing 104 causes a portion of the proximal end 148 of housing 104 to extend from a side of the elongated body 102 through the side opening 112 and outside of the elongated body 102. Further, pivoting of the housing 104 causes the distal opening of the first barrel 140 to be substantially aligned with distal opening 108 of the elongated body 102. As such, the first barrel 140 is exposed and accessible for receiving a tool and/or bone screw therein. In this position, the lumen of the first barrel 140 is also substantially aligned with the first fixation aperture 202*a*.

Figure 15:
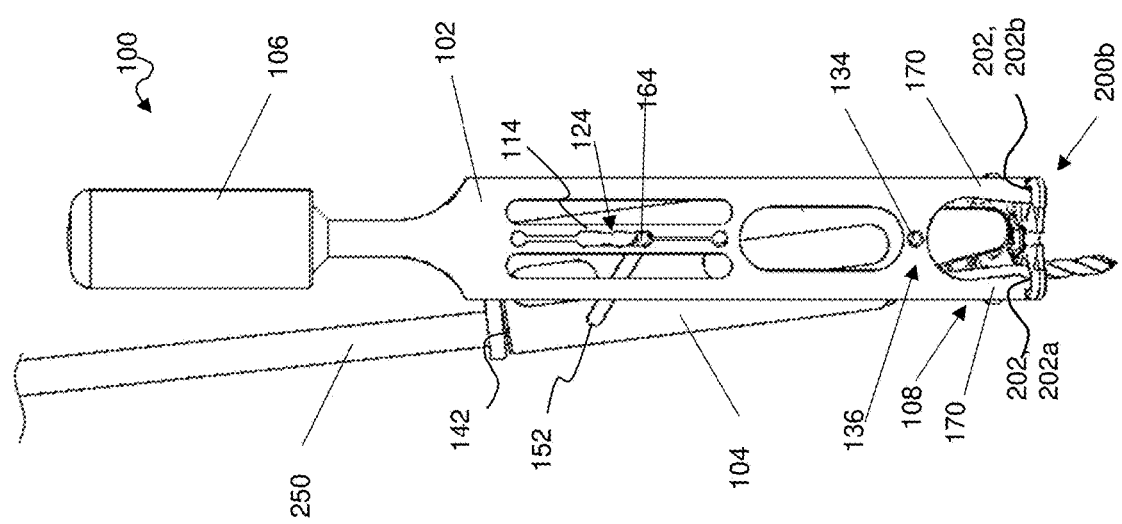
FIG. 15 shows a front plain view of FIG. 14.

In the first use position, a tool may be inserted through the first barrel 140 to prepare the bone for placement of the bone screw. As shown in FIG. 15, the tool (e.g., a drill) 250 is inserted into the first barrel 140 of the guide 100 while the guide 100 is in the first use position. Because the lumen of the first barrel 140 is in substantial alignment with the fixation aperture 202*a* of bone plate 200*b*, the tool 250 is also inserted through first fixation aperture 202*a* to prepare the bone for placement of the bone screw. Once the bone has been prepared to receive a fastener, the tool 250 may be removed and a first bone screw may be inserted through first barrel 140 of guide 100 into first fixation aperture 202*a*, e.g., via a driver (not shown).

Once the first bone screw has been inserted and/or fixated, the driver may be removed, and the process may be repeated for inserting a second bone screw into the second fixation aperture 202*b* of bone plate 200*b*. According to an exemplary embodiment, the housing 104 may be actuated to the second use position without removing the guide 100 from its position adjacent bone plate 200*b*. Specifically, the guide 100 may be actuated to the second use position (FIGS. 9-10) to allow the second bone screw (not shown) to be inserted into the second fixation aperture 202*b*. Actuation of the guide 100 to the second use position involves actuating the guide 100 such that second barrel 142 of the guide 100 is accessible to receive the second bone screw to be inserted into second fixation aperture 202*b*. Actuation of the guide 100 to the second use position includes actuating the actuator 106 such that the housing 104 pivots about the pivot point 136 making the second barrel 142 of the housing 104 accessible to receive the second bone screw to be inserted into the second fixation aperture 202*b*. Actuating the actuator 106 causes the drawbar 156 to linearly translate relative to the housing 104 and the elongated body 102. This also causes linear translation of the coupler 164 which is slidingly disposed within the slots 114, 152 in the elongated body 102 and the housing 104. The coupler 164 may slide from a position in the second locking feature 124*b* of the slot 114 in the elongated body 102 and a distal portion 152*b* of the slot 152 in the housing 104 to a position in the third locking feature 124*c* of the slot 114 and the proximal end 152*c* of the slot 152 in the housing 104. As a result of linear translation of the coupler 164 within the slots 114, 152, the housing 104 pivots relative to elongated body 102 about the pivot point 136. Pivoting of housing 104 causes a portion of the proximal end 148 of the housing 104 to extend from a side of the elongated body 102 through a side opening 112 and outside of the elongated body 102. Further, pivoting the housing 104 causes the distal opening of the second barrel 142 to be substantially aligned with distal opening 108 of the elongated body 102. As such, the lumen of the second barrel 142 is exposed and accessible for receiving a tool and/or bone screw therein. In this position, the lumen of the second barrel 142 is also substantially aligned with the second fixation aperture 202*b*.

In the second use position, a tool, e.g., tool 250, may be inserted through second barrel 142 to prepare the bone of placement of the bone screw. The tool 250 may be inserted into the second barrel 142 of the guide 100 while the guide 100 is in the second use position. Because the second barrel 142 is substantially aligned with the second fixation aperture 202b of bone plate 200b, the tool is also inserted through second fixation aperture 202b to prepare the bone for placement of the bone screw. Once the bone has been prepared, the tool 250 may be removed and the second bone screw may be inserted through the second barrel 142 of the guide 100 into the second fixation aperture 202b, e.g., via a driver (not shown). After the second bone screw has been inserted and/or fixated, the driver may be removed, and the entire method may be repeated for each subsequent pair of fixation apertures 202 until bone plate 200b the desired level of fixation is achieved.

Figure 17:
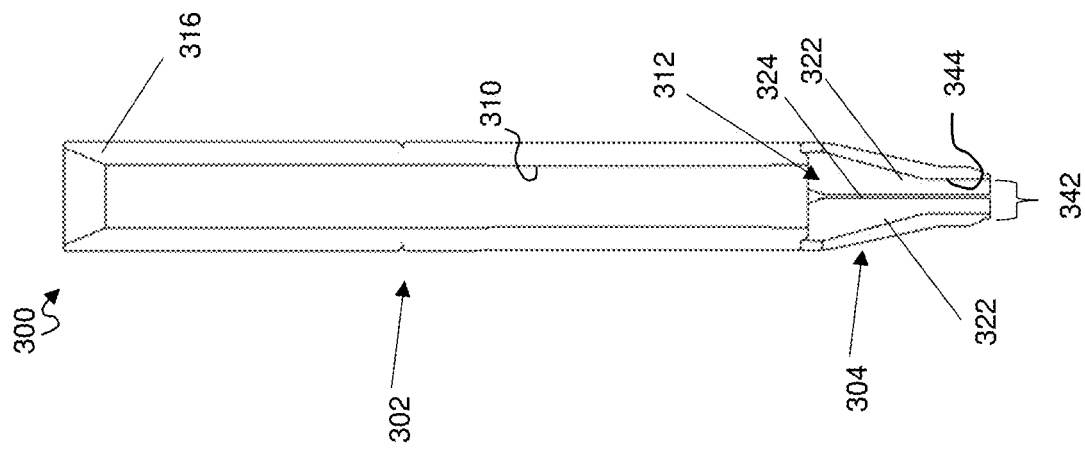
FIG. 17 shows a cross-sectional view of the surgical instrument of FIG. 16.
Figure 16:
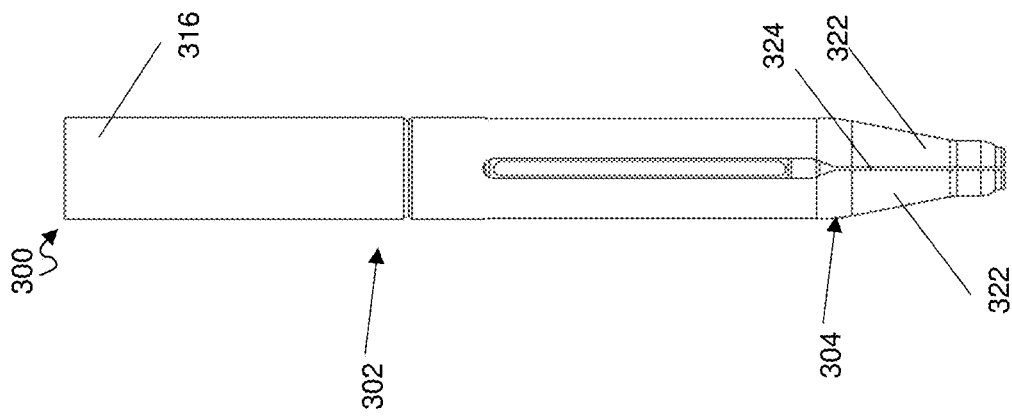
FIG. 16 shows a front plain view of a surgical instrument in an unexpanded configuration according to another embodiment of the disclosure.

FIGS. 16-17 illustrate an alternative embodiment of a surgical instrument 300. The surgical instrument 300 may include an elongated body 302 having a segmented distal tip 304 and a guide barrel 310 (FIG. 17) extending longitudinally within the elongated body 302. In some embodiments, elongated body 302 and the guide barrel 310 is composed of suitable materials known to those skilled in the art and include metal, such as stainless steel and titanium, and plastics. The lumen of the guide barrel 310 may be substantially aligned with a bore 312 (FIG. 17) within segmented distal tip 304. The guide barrel 310 may be sized and shaped to accommodate insertion and rotation of a tool, e.g., a drill, tap, awl, or driver, (not shown) therein. The guide barrel 310 has an opening at a proximal end 316 of elongated body 302 such that proximal end 316 may receive the tool therethrough. Further, the lumen of the guide barrel 310 is in communication with a bore 312 within segmented distal tip 304.

Figure 18:
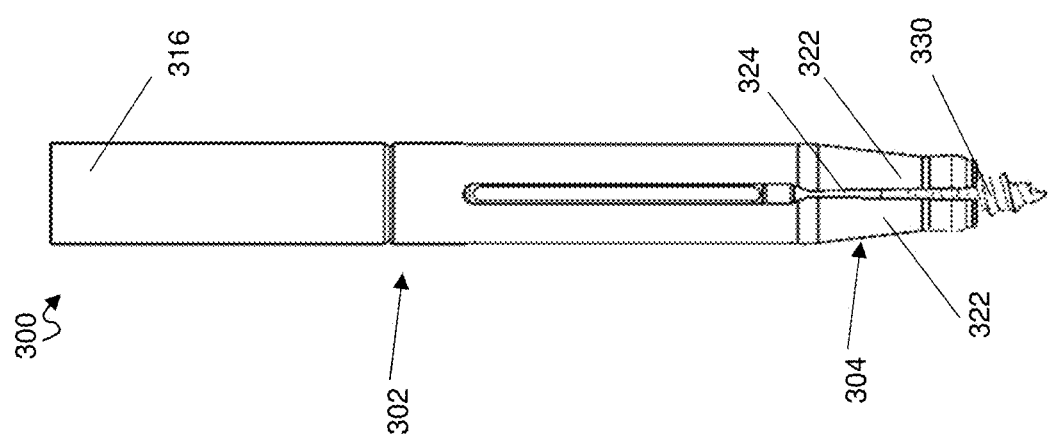
FIG. 18 shows a front plain view of the surgical instrument in an expanded configuration.

In some embodiments, segmented distal tip 304 includes at least one segment 322. In some embodiments, the segmented distal tip 304 includes a plurality of segments 322. The segments 322 may be defined within the segmented distal tip 304 by slots 324. That is, the slots 324 may be formed within segmented distal tip 304 to define segments 322 such that adjacent the segments 322 are separated by a slot 324. The segments 322 and the slots 324 may each extend longitudinally about a desired length of elongated body 302. The segmented distal tip 304 is configured to transition between an unexpanded configuration (FIG. 16) and an expanded configuration (FIG. 18). The segments 322 may be resilient such that the segments 322 can splay outward and/or deflect upon receiving some force and return substantially to their original position when the force is no longer provided. That is, the segments 322 are capable of being displaced and/or expanded when receiving some force.

In the unexpanded configuration (FIG. 16), the segments 322 are in a constricted and/or in a closed position that may inhibit or provide at least some resistance to passage of tools or implants therethrough. In the expanded configuration (FIG. 18), the segments 322 are in an open position that allows passage of tools or instruments therethrough. That is, in the expanded configuration, the segments 322 are spaced apart from one another more so than in the unexpanded configuration. Further, in the unexpanded configuration, the slots 324 have a first dimension, and in the expanded configuration, the slots 324 have a second dimension. The second dimension of the slots 324 is larger than the first dimension due to the increase in space between segments in the expanded configuration. As used herein, "dimension" may include at least one of length, breadth, depth, circumference or width. The segmented distal tip 304 may be configured to transition from the unexpanded configuration to the expanded configuration upon engagement of the segmented distal tip 304 by a tool or implant, such as a head of a bone screw 330 (FIGS. 18-19), that is inserted through the guide barrel 310 and the segmented distal tip 304.

Figure 19:
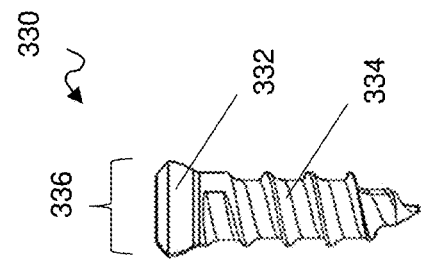
FIG. 19 shows a bone screw.

As shown in the exemplary embodiment illustrated in FIG. 19, the bone screw 330 may include a head 332 and a threaded shank 334. The threaded shank 334 may be configured to be inserted into bone, whereas the head 332 may be configured to be engaged by a tool, e.g., a driver, to drive bone screw 330 into bone as known in the art. An outer perimeter dimension or diameter 336 of the head 332 of bone screw 330 may be larger than a smallest inner dimension or diameter 342 (FIG. 17) of the bore 312 (FIG. 17) of the segmented distal tip 304. Therefore, because the bone screw 330 is being passed through the bore 312 and the head 332 that has a larger outer diameter 336 than smallest inner diameter 342 of the bore 312, the head 332 of the bone screw 330 will engage an inner surface 344 (FIG. 17) of the segments 322 of the segmented distal tip 304. As the head 332 of the bone screw 330 continues to pass through the bore 312 and engage the inner surface 344 of the segments 322, the head 332 of the bone screw 330 will force the segments 322 into the expanded configuration so that the bone screw 330 is able to pass through the segmented distal tip 304. Once the bone screw 330 is passed through the segmented distal tip 304 and the surgical instrument 300 is removed from being engaged with bone screw 330, the segments 322 are configured to return to an unexpanded configuration.

An exemplary method of use of the guide 300 may include positioning a bone plate having at least a first fixation aperture in a desired position relative to a bone. The bone plate may include, for example, the bone plates 200a, 200b illustrated in FIGS. 9-10. However, it is to be understood that the method is equally applicable to any conventional bone plate and/or other implants requiring fixation to a bone with fasteners. The bone plate 200b may include first aperture 202a and second fixation apertures 202b. The surgical instrument 300 may be inserted into the first fixation aperture 202a as shown in FIG. 20. Specifically, the segmented distal tip 304 may be inserted within first fixation aperture 202a. The surgical instrument 300 may be inserted into the first fixation aperture 202a in the unexpanded configuration. As shown in FIG. 21, a tool 350, e.g., a drill, may be inserted within the surgical instrument 300 to prepare the bone for insertion of the bone screw. Specifically, the tool 350 may be inserted through the guide barrel 310 (FIG. 17) and bore 312 (FIG. 17) into the first fixation aperture 202a to prepare the bone for insertion of the bone screw. After the bone is prepared, the tool 350 can be removed.

Figure 22:
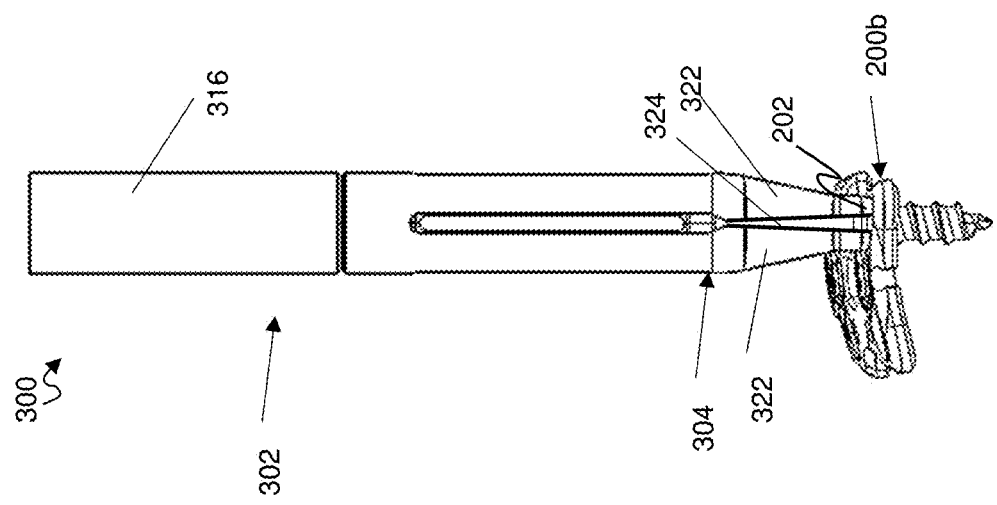
FIG. 22 shows a front plain view of the surgical instrument adjacent the bone plate with a bone screw inserted therein.
Figure 24:
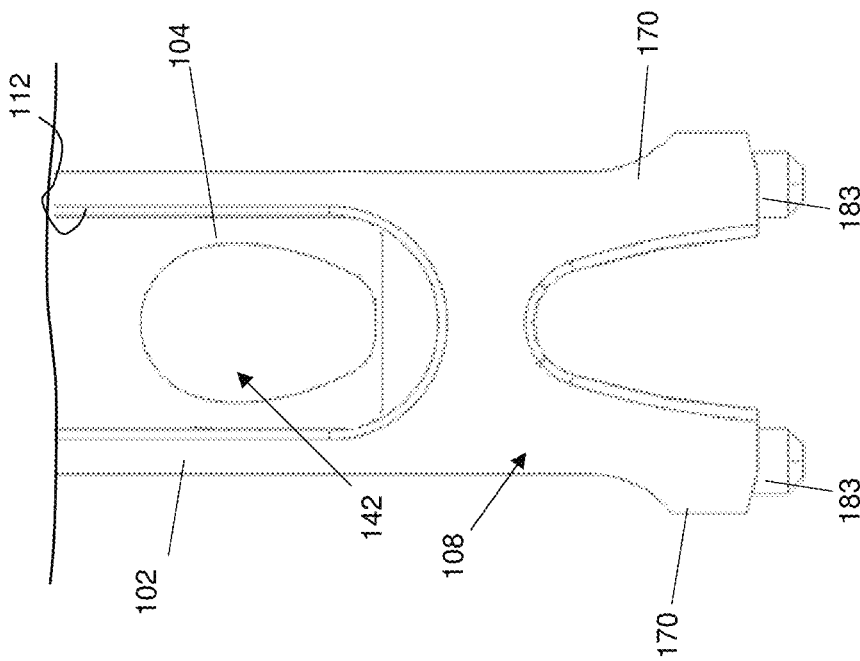
FIG. 24 shows an enlarged side plain view of the distal end of the elongated body of FIG. 1.
Figure 23:
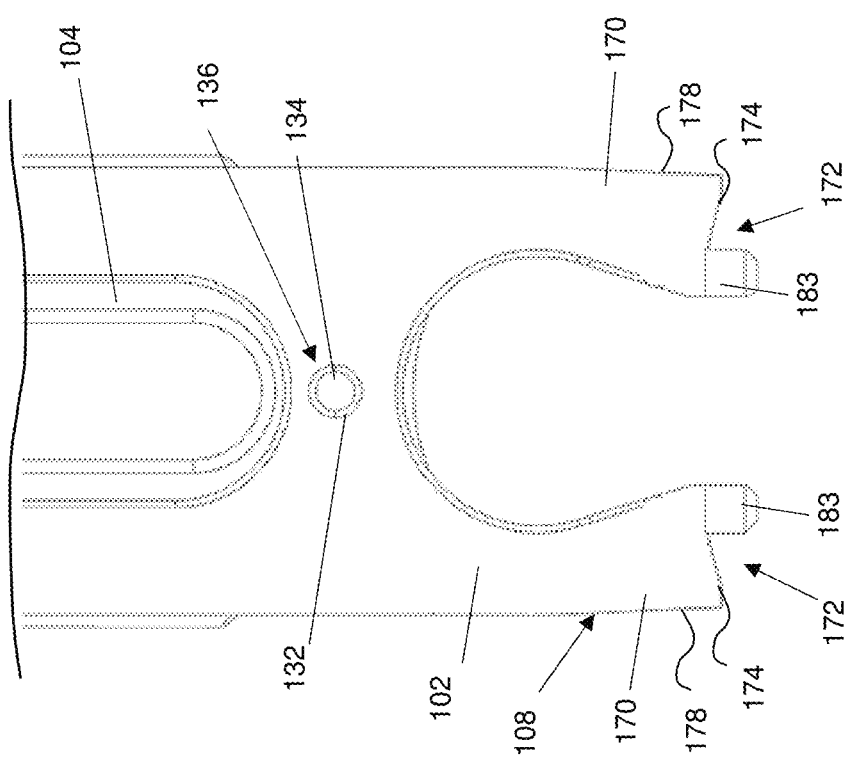
FIG. 23 shows an enlarged front plain view of the distal end of the elongated body according to another embodiment of the disclosure.

As illustrated in FIG. 22, a first bone fastener, e.g., bone screw 330, may be inserted through the surgical instrument 300. More specifically, bone screw 330 may be inserted through the guide barrel 310 (FIG. 17) and through bore 312 (FIG. 17) of the segmented distal tip 304. During insertion of the bone screw 330, the head 332 (FIG. 19) of bone screw 330 may engage with segments 322 of the segmented distal tip 304 such that segments 322 transition from an unexpanded configuration (FIGS. 16-17 and 20-21) to an expanded configuration (FIGS. 18 and 22). That is, as bone screw 330 is inserted through the first fixation aperture 202a and into the bone, segments 322 transition from the unexpanded configuration to the expanded configuration. During such transition and as bone screw 330 advances into first fixation aperture 202a, the segmented distal tip 304 disengages from the head 332 of bone screw 330. Segmented distal tip 304 is forced to disengage from the bone screw 330 and is forced out of or removed from first fixation aperture 202a of plate 200b. As a result, the segmented distal tip 304 returns to the unexpanded configuration.

While not specifically shown in the figures, this process may be repeated for a second fixation aperture 202b such that the method according to the disclosure may include inserting the segmented distal tip 304 of surgical instrument 300 into the second fixation aperture 202b, wherein segments 322 of segmented distal tip 304 are in the unexpanded configuration. Subsequently, a tool, e.g., tool 350, may be inserted into second fixation aperture 202b to prepare the bone for insertion of a second bone screw, e.g., bone screw 330. The second bone screw may be inserted within the guide barrel 310 (FIG. 17) and through bore 312 (FIG. 17) of the segmented distal tip 304. Insertion of the second bone screw may include engaging the segments 322 of segmented distal tip 304 with a head of the second bone screw with such that segments 322 transition from the unexpanded configuration to the expanded configuration. The method may further include inserting second bone screw within second fixation aperture 202b and into the bone. The method may also include removing segmented distal tip 304 of surgical instrument 300 from second fixation aperture 202b, wherein the segmented distal tip 304 disengages from the head of the second bone screw thereby returning to the unexpanded configuration. As should be understood, the method can be repeated for any additional fixation apertures within the bone plate.

Figure 25:
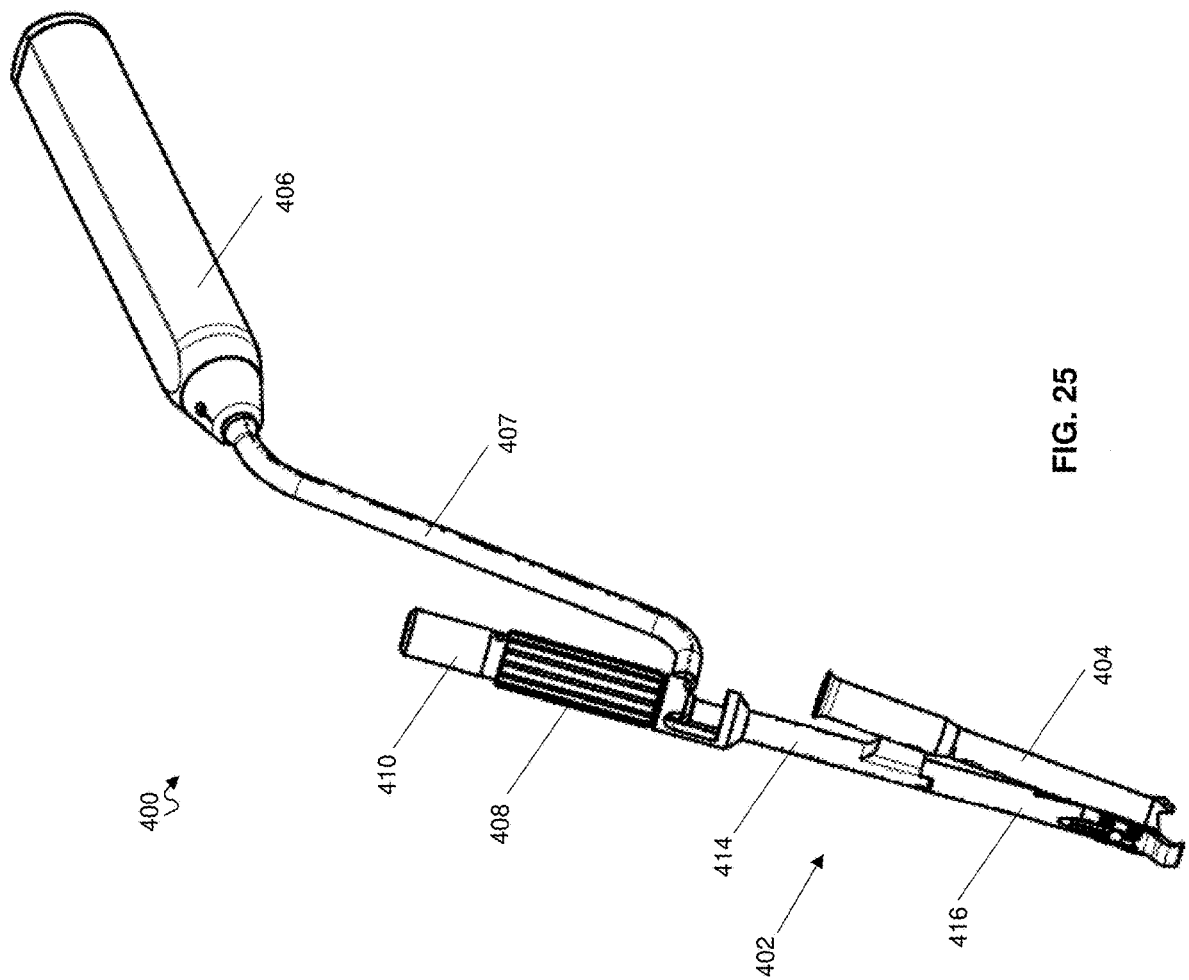
FIG. 25 shows a perspective view of a surgical instrument according to another embodiment of the disclosure.
Figure 26:
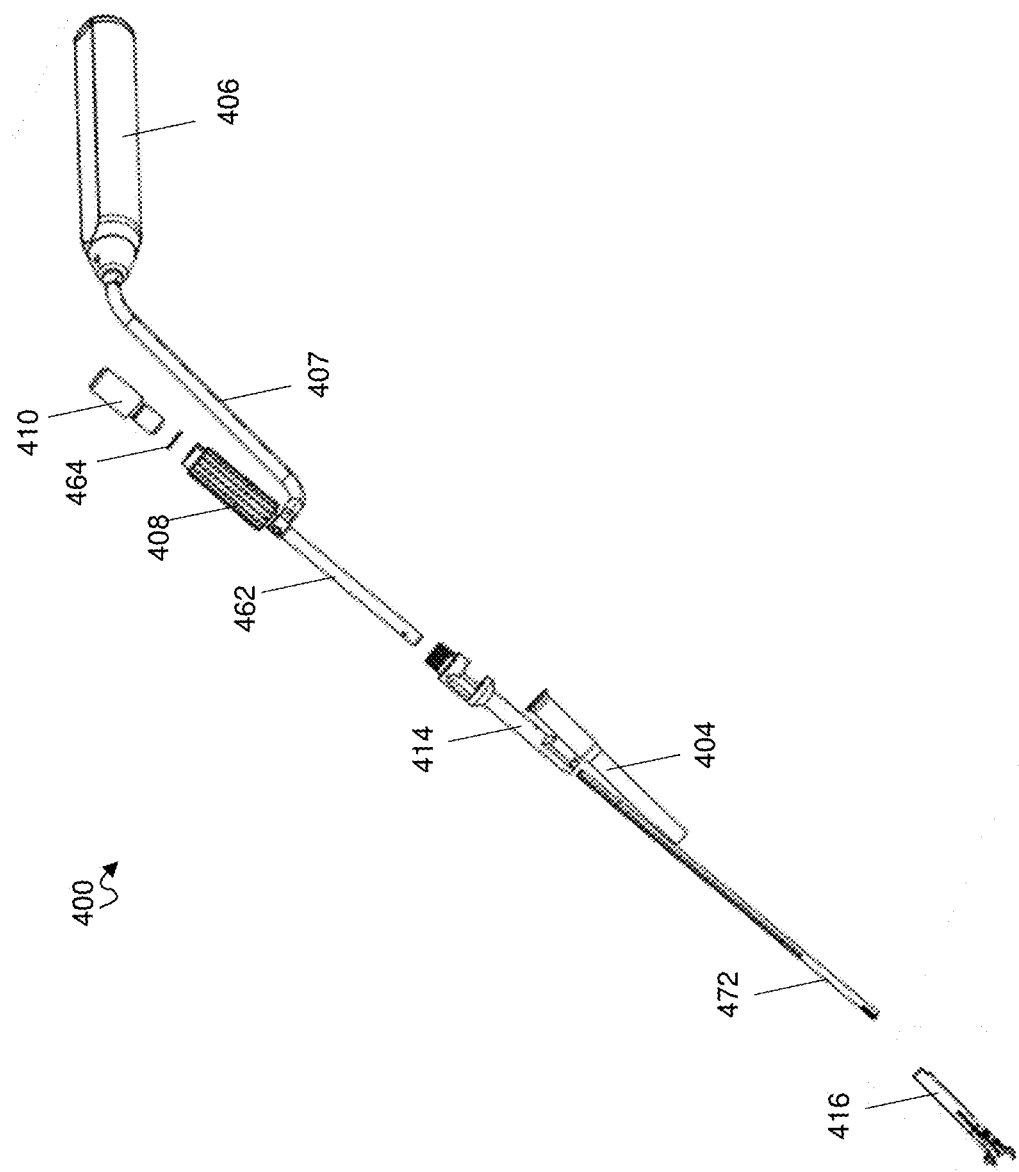
FIG. 26 shows an exploded perspective view of the surgical instrument according to the embodiment of FIG. 25.

FIGS. 25-26 show another embodiment of a surgical instrument 400 according to embodiments of the disclosure. The surgical instrument 400 may be a drill, tap and screw guide. As shown, the surgical instrument 400 includes an elongate body 402, a barrel 404, a handle 406, a handle connector 407, a first actuator 408, a second actuator 410. The elongate body 402 includes a proximal housing 414 and a distal housing 416. The proximal housing 414 is configured to rotate relative to the distal housing 416. The distal housing 416 is configured to engage a bone plate, e.g., an anterior cervical plate such as bone plates 200a, 200b (FIGS. 11-13). The barrel 404 is fixed to the proximal housing 414 and is therefore configured to rotate about the elongate body 402 relative to the distal housing 416 as the proximal housing 414 rotates. The barrel 404 is sized and shaped to receive drills, taps, and bone screws therein. The proximal housing 414 is fixed to the actuator 408 such that the actuator 408 controls rotation of the proximal housing 414, and thus, the barrel 404 thereby positioning the barrel 404 in various desired use positions as will be discussed herein. The actuator 410 controls locking and unlocking of the surgical instrument 400 to the bone plate as will be described herein. Specifically, the surgical instrument 400 can be locked to the cranial and caudal ends of the bone plate and used to prepare the bone and fix the bone screws at the cranial and caudal fixation apertures of the bone plate. The handle 406 is configured to be held by the user (e.g., a medical professional) during use. The handle connector 407 positions the handle at an angle and offset from the elongate body 402 such that the handle 406 is not in the viewing window of the user.

Figure 29:
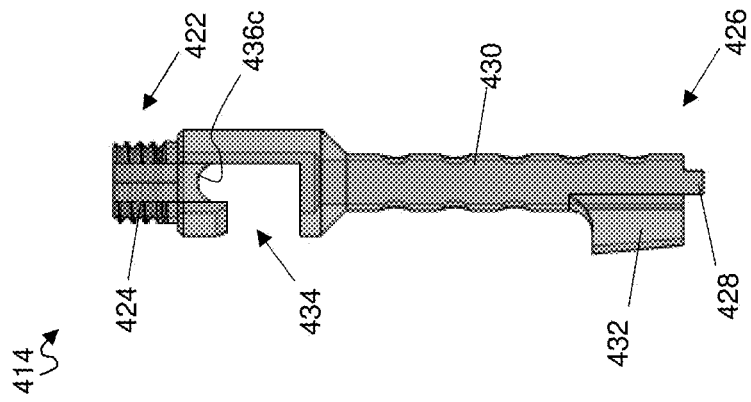
FIG. 29 shows a side view of the proximal housing according to embodiments of the disclosure 180° from the side view of FIG. 27.
Figure 28:
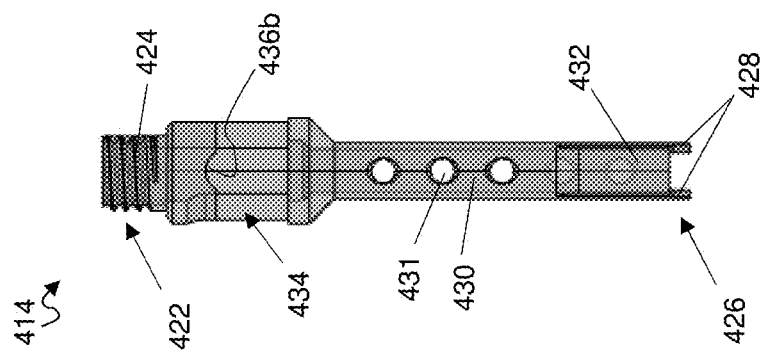
FIG. 28 shows a front view of the proximal housing according to embodiments of the disclosure 90° from the side view of FIG. 27.
Figure 27:
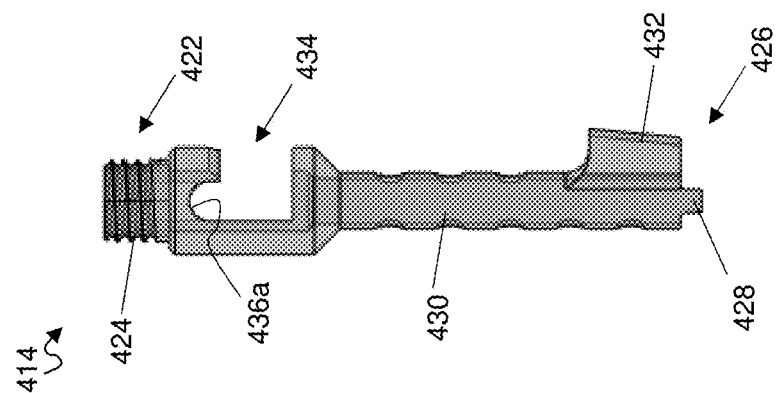
FIG. 27 shows a side view of the proximal housing according to embodiments of the disclosure.

Turning now to FIGS. 27-29, the proximal housing 414 is shown. The proximal housing 414 includes a first end 422 sized and shaped to fix to the actuator 408. In one example, (shown) the first end 422 can include threads 424 for threadingly engaging with the actuator 408. While threads are shown, the proximal housing 414 can fix to the actuator 408 via any other now known or later developed means such as, for example, a snap fit connection or mating interface connection. The proximal housing 414 also includes a second end 426 sized and shaped to mate with the distal housing 416 (FIGS. 25-26 and 30-32). As shown, the second end 426 can include tabs or tangs 428 for mating with corresponding cutouts or recesses 444 (FIGS. 30-32) formed within the distal housing 416. Extending between the first end 422 and the second end 426 is the body 430 of the proximal housing 414. The body 430 is substantially hollow for accommodating other components of the surgical instrument 400 as will be described herein. As shown, the body 430 can have various openings or apertures 431 to facilitate sterilization and/or cleaning procedures. Positioned proximally of the tabs 428 is an extension 432 for fixing the barrel 404 (FIGS. 25-26) thereto. The extension 432 allows for the barrel 404 to be positioned an angle relative to the body 430 of the proximal housing 414. Further, the proximal housing 414 includes an opening 434 for enabling the proximal housing 414 to rotate about the handle connector 407 as will be described herein. The opening 424 may have engagement surfaces 436a, 436b, 436c for engaging with the handle connector 407 and maintaining a position of the proximal housing 414 in the various use positions.

Figure 32:
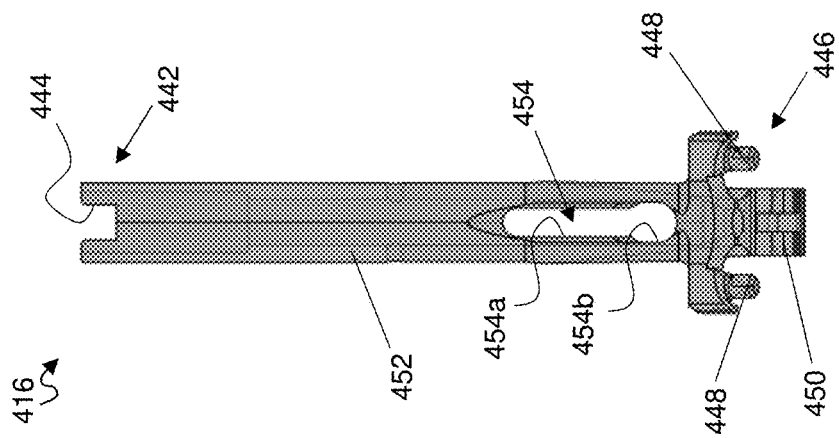
FIG. 32 shows a side view of the distal housing according to embodiments of the disclosure 180° from the side view of FIG. 30.
Figure 31:
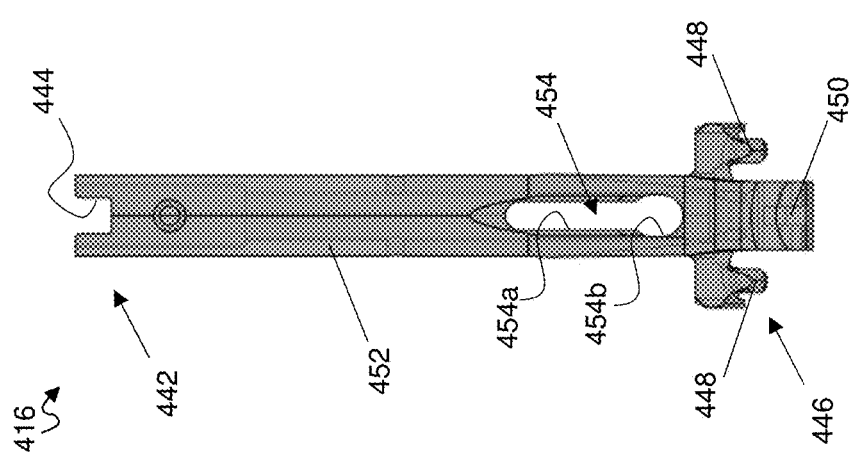
FIG. 31 shows a front view of the distal housing according to embodiments of the disclosure 90° from the side view of FIG. 30.
Figure 30:
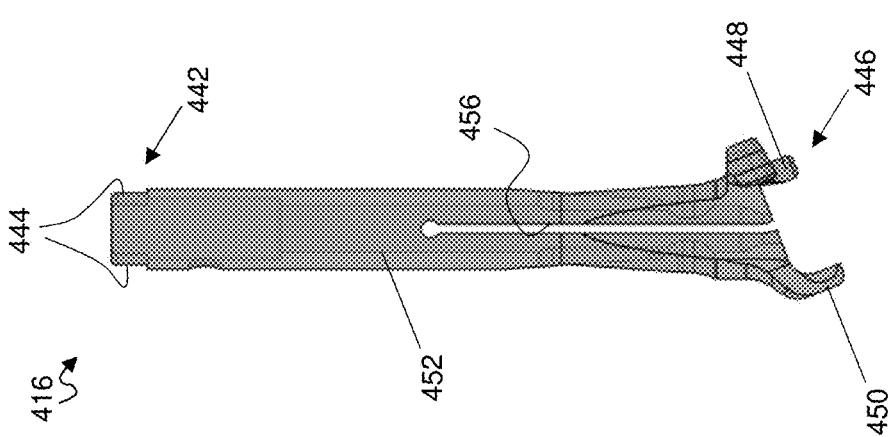
FIG. 30 shows a side view of the distal housing according to embodiments of the disclosure.

Turning now to FIGS. 30-32, the distal housing 416 is shown. The distal housing 416 includes a first end 442 configured to mate with the proximal housing 414 (FIGS. 27-29). As shown, the first end 442 can include cutouts or recesses 444 for matingly engaging with tabs 428 (FIGS. 27-29) of the proximal housing 414. However, while tabs 428 and cutouts 444 are shown, any other now known or later developed means for coupling the proximal housing 414 and the distal housing 416 while allowing the proximal housing 414 to rotate thereto can be used without departing from the disclosure. The distal housing 416 also includes a second end 446 having at least one pin 448 (two shown) for engaging docking pin holes on a bone plate and a gripping member or lip 450 configured to wrap around a side of the bone plate and engage with an underside or bone-facing surface of the bone plate. Extending between the first and second ends 442, 446 is the body 452 of the distal housing 416. The body 452 is substantially hollow. A groove 454 is formed within the body 452 proximally of the second end 446. As shown, the groove 454 is formed on opposing front and back sides of the body 452. The groove 454 includes a narrow portion 454a and a wide portion 454b. As will be described herein, the groove 454 accommodates the coupler 455 (FIG. 34-35c) therein. The coupler 455 couples the distal housing 416 to a drawbar 472 (FIGS. 33-35c). As will be described herein, the distal housing 416 also includes a ramp 457 (FIGS. 35a-35c) within the groove 454 that the coupler 455 travels along when the drawbar 472 moves proximally and distally. A slit 456 is also formed on opposing sides of the body 452 (positioned approximately 90° of the groove 454). The slit 456 enables distal housing 416 to expand to accommodate transitioning between locked and unlocked states as will be described herein.

Figure 33:
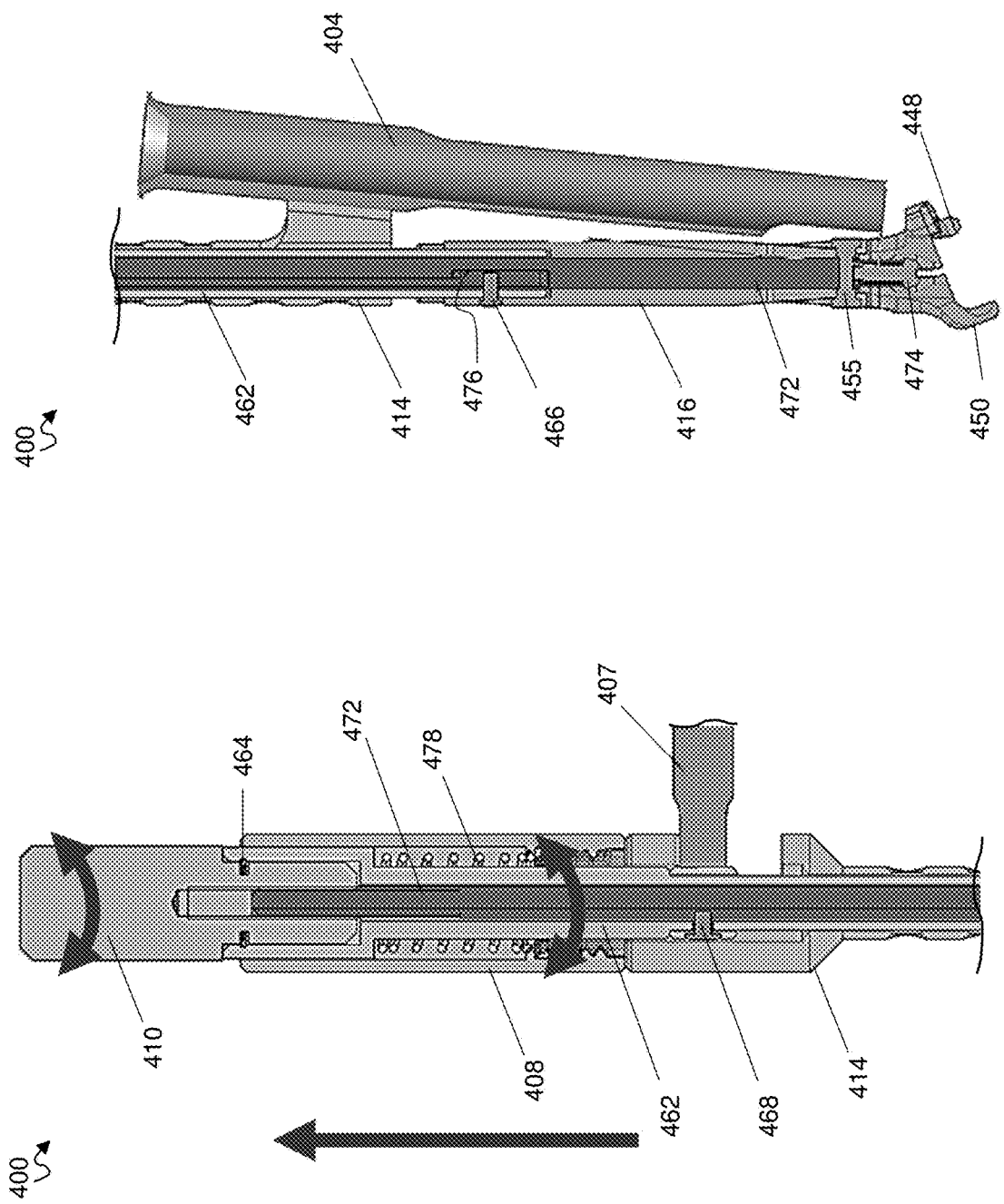
FIG. 33 shows an enlarged cross-sectional view of a proximal end of the surgical instrument according to the embodiments of FIG. 25.

Turning now to FIG. 33, an enlarged cross-sectional view of the actuators 408, 410 is shown. The actuator 408 is configured to cause transitioning of the surgical instrument 400 between various use positions, and more specifically, the actuator 408 is operatively associated with the proximal housing 414 such that the proximal housing rotates relative to the distal housing 416 upon rotation of the actuator 408. The actuator 410 is positioned proximally to the actuator 408. The actuator 410 is configured to cause locking and unlocking of the distal housing 416 relative to the bone plate.

Figure 34:
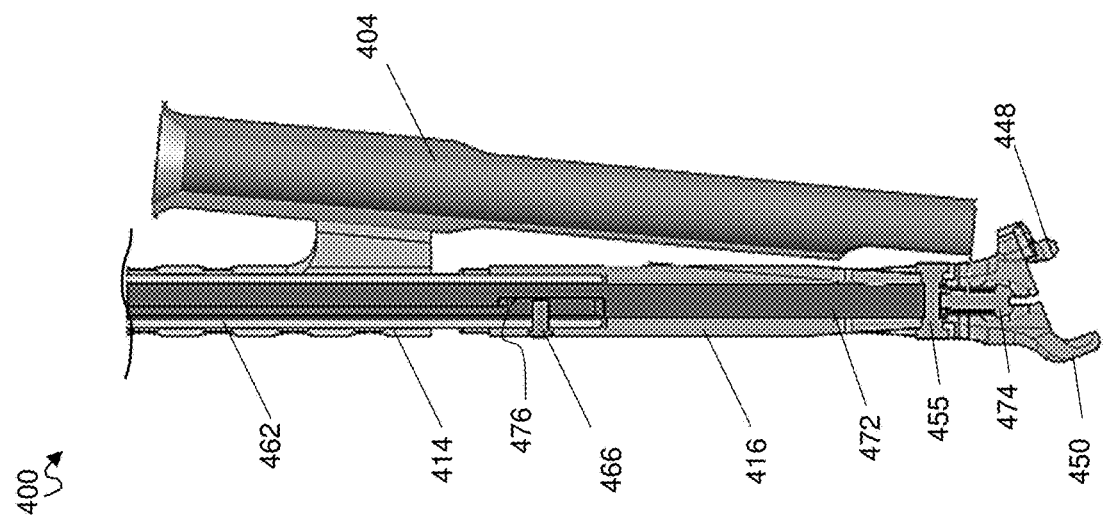
FIG. 34 shows an enlarged cross-sectional view of a distal end of the surgical instrument according to the embodiments of FIG. 25.

As shown, the surgical instrument 400 also includes an inner housing 462 coupled to the actuator 410 via an o-ring 564 that sits within a circumferential groove formed within the actuator 410. Such a configuration allows the actuator 410 to rotate relative to the inner housing 462. The inner housing 462 extends longitudinally within the actuator 408, the proximal housing 414 and the distal housing 416. The actuator 408 and the proximal housing 414 are configured to translate and rotate about the inner housing 462. Turning to FIG. 34, a distal end of the inner housing 462 is coupled to the distal housing 416 via a pin 466 such that the inner housing 462 is fixed to the distal housing 416. Another pin 468 (FIG. 33) couples the inner housing 462 to the handle connector 407 (FIG. 33) such that the inner housing 452 is fixed to the handle connector 407, and thus the handle 406.

The surgical instrument 400 also includes a drawbar 472 extending longitudinally within the inner housing 462. The drawbar 472 is configured to move proximally or distally within the elongate body 402 (or more specifically, within the proximal housing 414 and distal housing 416) upon actuation of the actuator 410. As best seen in FIG. 35, a distal end of the drawbar 472 includes an engagement member 474 configured to abut against a pair of opposed inwardly facing surfaces 475 (FIGS. 35*a*-35*c*) of the distal end of the distal housing 416. In some embodiments, the engagement member 474 may be the distal tip of the drawbar 472. In other embodiments, the engagement member 474 may be a separate component fixed to a distal end of the drawbar 472. A proximal end of the drawbar 472 may be threadedly connected to the actuator 410 such that rotation of the actuator 410 (as shown by the arrow) causes translational movement of the drawbar 472 relative to the actuator 410. For example, rotation of the actuator 410 in one direction (i.e., clockwise or counterclockwise direction) causes the drawbar 472 to move in the distal direction such that the engagement member 474 or the distal tip of the drawbar 472 abuts the inwardly facing surfaces 475 of the distal housing 416 to push the inwardly facing surfaces 475 apart to cause expansion of the distal housing 416 about the slit 456 of the distal housing 416 to allow unlocking of the surgical instrument from the bone plate. Rotation of the actuator 410 in another direction (i.e., the other one of the clockwise or the counterclockwise direction) causes the drawbar 472 to move in the proximal direction such that the engagement member 474 or distal tip of the drawbar 472 disengages from the inwardly facing surfaces 475 of the distal housing 416 thereby causing contraction of the distal housing 416 about the slit 456 and/or repositioning of the distal housing 416 in the resting state to lock the distal housing 416 relative to the bone plate. Together, the gripping member 450 and the docking pins 448 lock the surgical instrument 400 to the bone plate.

A pin 455 operatively couples the drawbar 472 to the distal housing 416. The pin 455 translates with the drawbar 472 upon actuation of the actuator 410. The pin 455 translates within the groove 454 (FIGS. 31-32) of the distal housing 416 and along the ramps 457 formed within the distal housing 416 within the groove 454. As the pin 455 and the drawbar 472 move distally (FIG. 35*b*), the engagement member 474 abuts the inwardly facing surfaces 475 thereby pushing the inwardly facing surfaces 475 apart such that the distal housing 416 expands about the slit 456 (FIG. 30). As a result, the surgical instrument 400 is in an unlocked state allowing the user the ability to engage and disengage the bone plate with the surgical instrument 400. As the pin 455 and the drawbar 472 move proximally (FIG. 35*c*), the engagement member 474 disengages from and/or is not in engagement with the inwardly facing surfaces 475. As a result, the distal housing 416 of the surgical instrument 400 returns to a non-expanded or resting state. At this point, the surgical instrument 400 is in a locked state and maintains a position of the surgical instrument 400 relative to the bone plate. The pin 455 also enables the user the ability to confirm that the surgical instrument 400 is locked or unlocked relative to the bone plate by viewing the location of the pin 455 within the groove 454. The drawbar 472 also includes a groove or cutout 476 (FIG. 34) positioned between the proximal and distal ends to accommodate the pin 466 that couples the inner housing 462 and the distal housing 416 such that the pin 466 translates within the groove 476 as the drawbar 472 to moves proximally and distally upon actuation of the actuator 410.

Returning to FIG. 33, the proximal housing 414 is fixed to the actuator 408. The actuator 408 is configured to move in the proximal direction (as shown by the arrow) and to be rotated (as shown by the arrows) in order to cause rotation of the proximal housing 414. A biasing element 478 is positioned within the actuator 408 and engages the first end 432 of the proximal housing 414. The biasing element 478 is configured to bias the proximal housing 414 distally. When the actuator 408 is actuated, the biasing force of the biasing element 478 is overcome to cause rotation of the proximal housing. In use, the user (e.g., a medical professional), pulls the actuator 408 in the proximal direction, thereby causing the proximal housing 414 to also move in the proximal direction and compress the biasing element 478. This lifts the respective engagement surface 436*a*, 436*b*, 436*c* of the opening 436 within the proximal housing 414 off of the handle connector 407 and disengages the tabs 428 of the proximal housing 414 from the cutouts 444 of the distal housing 416. This movement allows the user the ability to then rotate the actuator 408 to another use position about the handle connector 407. Once in the desired position, the user releases the actuator 408 or allows the actuator 408 to position in a resting state such that the biasing element 478 causes the proximal housing 414 to move distally. This results in the respective engagement surface 436*a*, 436*b*, 436*c* corresponding to the desired use position to then rest against the handle connector 407 and re-engagement of the tabs 428 with the distal housing 416.

FIGS. 36-38 show the surgical instrument 400 in a first barrel use position. Specifically, FIG. 36 shows a front view of the surgical instrument 400 in the first barrel use position, FIG. 37 shows the front view of the surgical instrument 400 with the handle 406 and handle connector 407 removed for clarity, and FIG. 38 shows a side the surgical instrument 400 (i.e., rotated 90°) with only a portion of the handle connector 407 showing. This position can be used to align the barrel 404 with a first fixation aperture of the bone plate. In this position, the barrel 404 is positioned to the left of the handle 406 (FIG. 36) on the page of the drawing. Further, the tabs 428 (FIG. 37) of the proximal housing 414 are resting within and/or engaged with the cutouts 444 (FIG. 37) of the distal housing 416. The engagement surface 436*c* is resting against and/or engaged with the handle connector 407.

FIGS. 39-41 show the surgical instrument 400 in an insertion position. Specifically, FIG. 39 shows a front view of the surgical instrument 400 in the insertion position, FIG. 40 shows the front view of the surgical instrument 400 with the handle 406 and handle connector 407 removed for clarity, and FIG. 41 shows a side the surgical instrument 400 (i.e., rotated 90°) with only a portion of the handle connector 407 showing. In this position, the barrel 404 is aligned with the handle connector 406 resulting in an overall lower profile in this position which can maximize in visualization during insertion of the instrument. This position can be used to insert the surgical instrument within the operative corridor. Further, the tabs 428 of the proximal housing 414 are not aligned with the cutouts 444 of the distal housing 416. Instead, the tabs 428 are resting on a proximal end surface of the distal housing 416. The engagement surface 436b is resting against and/or engaged with the handle connector 407.

FIGS. 42-44 show the surgical instrument 400 in a second barrel use position. Specifically, FIG. 42 shows a front view of the surgical instrument 400 in the second barrel use position, FIG. 43 shows the front view of the surgical instrument 400 with the handle 406 and handle connector 407 removed for clarity, and FIG. 43 shows a side the surgical instrument 400 (i.e., rotated 90°) with only a portion of the handle connector 407 showing. This position can be used to align the barrel 404 with a second fixation aperture of the bone plate, adjacent the first fixation aperture. The barrel 404 is positioned 180° from the position of the barrel 404 in the first barrel use position (FIGS. 36-38). In this position, the barrel 404 is positioned to the right of the handle 406 (FIG. 42) on the page of the drawing. Further, the tabs 428 (FIG. 43) of the proximal housing 414 are resting within and/or engaged with the cutouts 444 (FIG. 43) of the distal housing 416. The engagement surface 436a is resting against and/or engaged with the handle connector 407.

Figure 45:
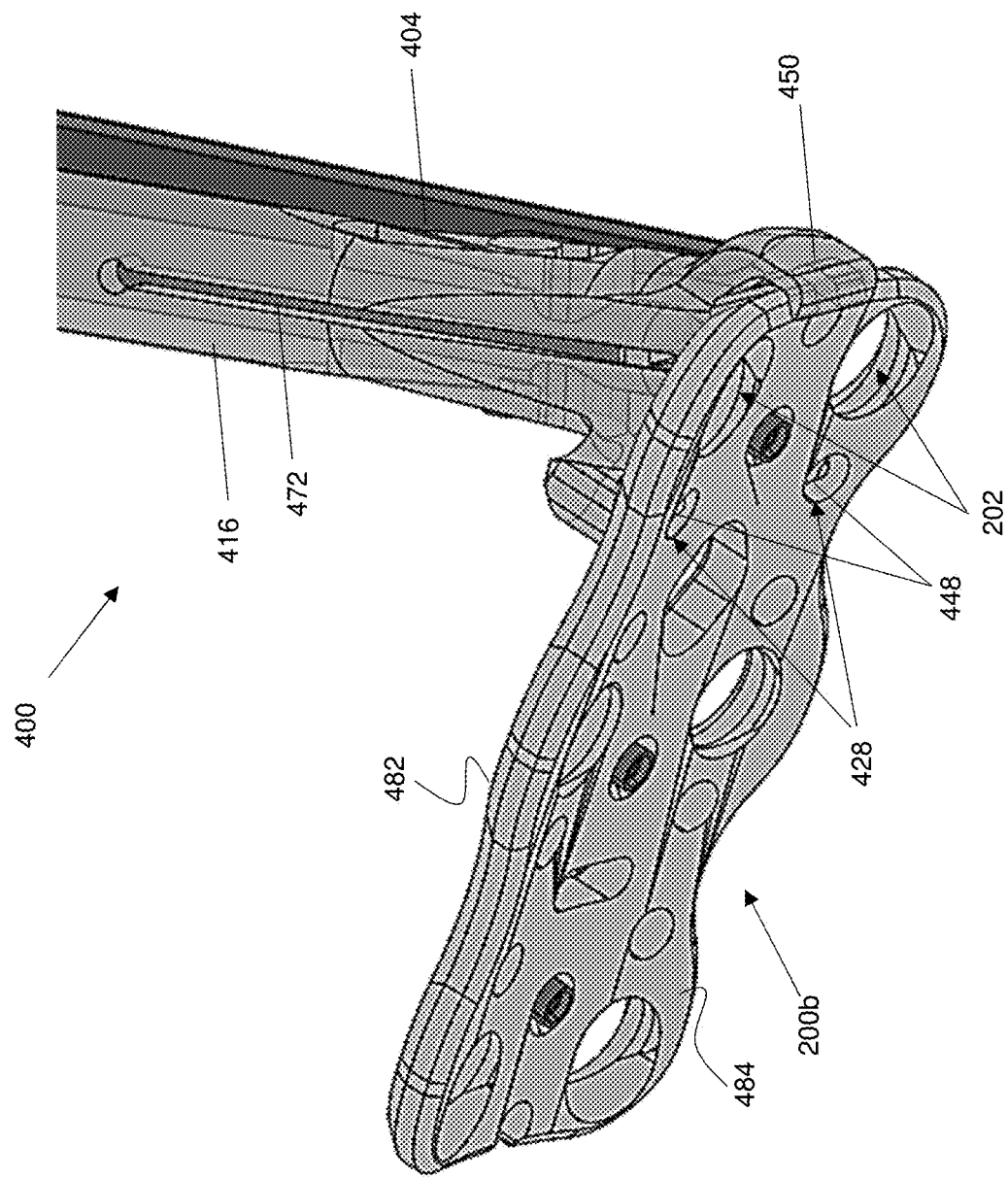
FIG. 45 shows a perspective view of the surgical instrument according to FIG. 25 engaged with a bone plate.

FIG. 45 shows a perspective view of the surgical instrument 400 engaging a bone plate 202b. As shown, the pins 448 are positioned within docking pin holes 228 of the bone plate 202b. The gripping member 450 wraps around the bone plate 202b from a non-bone-facing side 482 (where the bone plate 202b is an anterior cervical plate, this is the anterior side) to a bone-facing side 484 (where the bone plate 202b is an anterior cervical plate, this is the posterior side).

FIGS. 46-48 show the surgical instrument 400 in the unlocked state. More specifically, FIG. 46 shows a front view of the surgical instrument 400 in the unlocked state, FIG. 47 shows a cross-sectional view of FIG. 46, and FIG. 48 shows an enlarged view of the distal end of the surgical instrument 400 of FIG. 47. As shown, the proximal end of the drawbar 472 is positioned distally within the actuator 410. Thus, the engagement member 474 is positioned distally relative to the distal end of the distal housing 416. Additionally, the pin 455 is positioned distally within the groove 454 of the distal housing 416, or more specifically, within the narrow portion 454a (FIGS. 31 and 32) of the groove 454. In this state, the engagement member 474 abuts the inwardly facing surfaces 475 (FIG. 35b) to cause expansion of the distal housing 416 such that the distal housing 416 can be engaged and disengaged from the bone plate.

Figure 51:
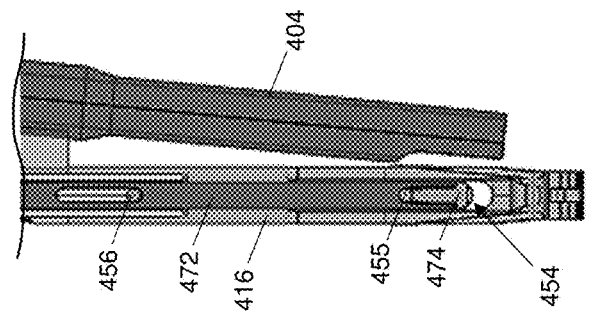
FIGS. 49-51 show the surgical instrument in the locked state where
Figure 50:
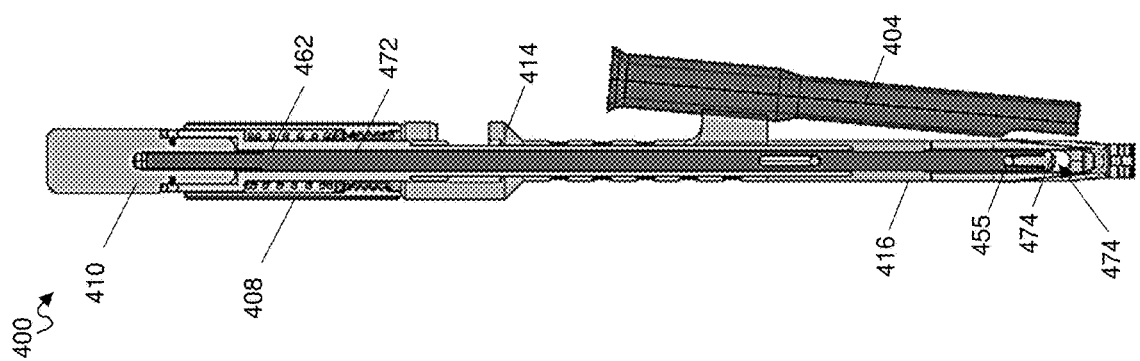
Figure 49:
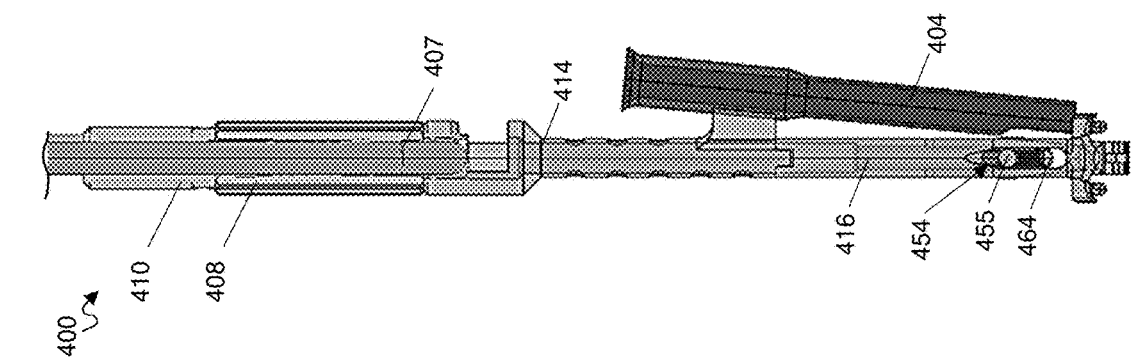

FIGS. 49-51 show the surgical instrument 400 in the locked state. More specifically, FIG. 49 shows a front view of the surgical instrument 400 in the locked state, FIG. 48 shows a cross-sectional view of FIG. 49, and FIG. 51 shows an enlarged view of the distal end of the surgical instrument 400 of FIG. 49. As shown, the proximal end of the drawbar 472 is positioned proximally within the actuator 410. Thus, the engagement member 474 is positioned proximally relative to the distal end of the distal housing 416. Additionally, the pin 455 is positioned proximally within the groove 454 of the distal housing 416, or more specifically, within the wide portion 454b (FIGS. 31 and 32) of the groove. In this state, the engagement member 474 does not abut the inwardly facing surfaces 475 (FIG. 35b), thus the distal housing 416 is in a resting or nonexpanded state such that the distal housing 416 can be locked to the bone plate.

Aspects of the disclosure also include a method. The method includes positioning a bone plate having a first fixation aperture and a second fixation aperture in a desired position relative to a bone. The method also includes positioning a guide or surgical instrument 400 in an unlocked state adjacent the bone plate at the first and second apertures. The surgical instrument 400 can be positioned at one of the cranial and caudal ends of the bone plate. Specifically, pins 448 of the surgical instrument 400 can be docked within docking pin holes of the bone plate. The surgical instrument 400 is then locked to the bone plate. More specifically, the actuator 410 can be actuated thereby causing the distal housing 416 to lock to the bone plate. During actuation of the actuator 410, the drawbar 472 is moved proximally such that a distal tip or engagement member 474 of the drawbar 472 disengages from the inwardly facing surfaces 475 of the distal housing 416. The gripping member 450 in this position engages with the bone-facing side of the bone plate. The surgical instrument 400 is then positioned in a first barrel use position that allows a first bone screw to be inserted into the first fixation aperture of the bone plate. Specifically, the actuator 408 can be actuated to cause the proximal housing 414 and the barrel 404 to position in the first use position such that the barrel 404 is aligned with the first fixation aperture of the bone plate.

The method also includes preparing the bone using the surgical instrument 400 for a bone screw. Specifically, a drill and tap can each be inserted within the barrel 404 to prepare the bone as is known in the art. Subsequently, the method includes inserting a bone screw into the barrel 404 while the barrel is in the first use position and through the first fixation aperture into the prepared bone. Next, the actuator 408 can be actuated to cause the proximal housing 414 and the barrel 404 to position in the second use position such that the barrel 404 is aligned with the second fixation aperture of the bone plate. The method also includes preparing the bone using the surgical instrument 400 for a bone screw. Specifically, a drill and tap can each be inserted within the barrel 404 to prepare the bone as is known in the art. Subsequently, the method includes inserting a bone screw into the barrel 404 while the barrel is in the second use position and through the second fixation aperture into the prepared bone. Once the bone screws have been inserted, the method includes unlocking the surgical instrument 400 from the bone plate. This can be accomplished by actuating the actuator 410 such that the drawbar 472 moves distally and the distal tip or engagement member 474 of the drawbar 472 abuts the inwardly facing surfaces 475 of the distal housing 416 to cause expansion of the distal housing 416 to allow the distal housing 416 can be disengaged from the bone plate. The surgical instrument 400 can then be moved to another location about the bone plate (e.g., the other one of the cranial or caudal ends of the bone plate) and the process can be repeated until all the desired screws are inserted therein. To prepare the bone and insert bone screws within the fixation apertures positioned between the cranial and caudal ends, one of the other surgical instruments 100, 300 described herein can be used.

In the descriptions above and in the claims, phrases such as "at least one of" or "one or more of" may occur followed by a conjunctive list of elements or features. The term "and/or" may also occur in a list of two or more elements or features. Unless otherwise implicitly or explicitly contradicted by the context in which it is used, such a phrase is intended to mean any of the listed elements or features individually or any of the recited elements or features in combination with any of the other recited elements or features. For example, the phrases "at least one of A and B;" "one or more of A and B;" and "A and/or B" are each intended to mean "A alone, B alone, or A and B together." A similar interpretation is also intended for lists including three or more items. For example, the phrases "at least one of A, B, and C;" "one or more of A, B, and C;" and "A, B, and/or C" are each intended to mean "A alone, B alone, C alone, A and B together, A and C together, B and C together, or A and B and C together." Use of the term "based on," above and in the claims is intended to mean, "based at least in part on," such that an unrecited feature or element is also permissible.

The terminology used herein is for the purpose of describing particular embodiments only and is not intended to be limiting of the disclosure. As used herein, the terms "first," "second," and the like, do not denote any order, quantity, or importance, but rather are used to distinguish one element from another, and the terms "a" and "an" herein do not denote a limitation of quantity, but rather denote the presence of at least one of the referenced item. It will be further understood that the terms "comprises" and/or comprising," when used in this specification, specify the presence of stated features, integers, steps, operations, elements, and/or components, but do not preclude the presence or addition of one or more other features, integers, steps, operations, elements, components, and/or groups.

The implementations set forth in the foregoing description do not represent all implementations consistent with the subject matter described herein. Instead, they are merely some examples consistent with aspects related to the described subject matter. Although a few variations have been described in detail herein, other modifications or additions are possible. In particular, further features and/or variations can be provided in addition to those set forth herein. For example, the implementations described above can be directed to various combinations and sub-combinations of the disclosed features and/or combinations and sub-combinations of one or more features further to those disclosed herein. In addition, the logic flows depicted in the accompanying figures and/or described herein do not necessarily require the particular order shown, or sequential order, to achieve desirable results. The scope of the following claims may include other implementations or embodiments.

What is claimed is:

1. A surgical instrument comprising:
    an elongate body having a proximal housing and a distal housing, the proximal housing configured to rotate relative to the distal housing and the distal housing configured to engage a bone plate;
    a barrel fixed to the proximal housing configured to rotate about the elongate body with rotation of the proximal housing;
    a first actuator engaged with the proximal housing and operably associated with the proximal housing such that the proximal housing rotates relative to the distal housing upon actuation of the first actuator, and
    a biasing element positioned within the first actuator and engaging a proximal end of the proximal housing, the biasing element configured to bias the proximal housing distally.

2. The surgical instrument of claim 1, wherein the proximal housing is fixed to the first actuator.

3. The surgical instrument of claim 1, wherein the first actuator is configured to move in a proximal direction and be rotated in order to cause rotation of the proximal housing.

4. The surgical instrument of claim 1, wherein actuation of the first actuator includes overcoming a biasing force of the biasing element to cause rotation of the proximal housing.

5. The surgical instrument of claim 1, further comprising:
    a second actuator positioned proximal to the first actuator, the second actuator configured to causing locking and unlocking of the distal housing relative to the bone plate.

6. The surgical instrument of claim 5, further comprising a drawbar configured to move proximally or distally within the elongate body upon actuation of the second actuator.

7. The surgical instrument of claim 6,
    wherein actuation of the drawbar in the proximal direction causes the distal housing to lock relative to the bone plate; and
    wherein actuation of the drawbar in the distal direction causes expansion of the distal housing to unlock the distal housing relative to the bone plate.

8. The surgical instrument of claim 1, wherein the distal housing includes a gripping member for engaging a bone-facing side of the bone plate.

9. A surgical instrument comprising:
    an elongate body having a proximal housing and a distal housing, the proximal housing configured to rotate relative to the distal housing and the distal housing configured to engage a bone plate;
    a barrel fixed to the proximal housing configured to rotate about the elongate body with rotation of the proximal housing;
    a first actuator positioned proximal to the proximal housing, the first actuator configured to causing locking and unlocking of the distal housing relative to the bone plate, and
    a second actuator engaged with the proximal housing and operably associated with the proximal housing such that the proximal housing rotates relative to the distal housing upon actuation of the second actuator.

10. The surgical instrument of claim 9, further comprising a drawbar configured to move proximally or distally within the elongate body upon actuation of the first actuator.

11. The surgical instrument of claim 10, wherein actuation of the drawbar in the proximal direction causes the distal housing to lock relative to the bone plate.

12. The surgical instrument of claim 11, wherein actuation of the drawbar in the distal direction causes expansion of the distal housing to unlock the distal housing relative to the bone plate.

13. The surgical instrument of claim 9, wherein the first actuator is configured to be rotated in order to cause locking and unlocking of the distal housing relative to the bone plate.

14. The surgical instrument of claim 9, wherein the distal housing includes at least one pin for docking within pin holes on the bone plate.

15. The surgical instrument of claim 9, wherein the distal housing includes a gripping member for engaging a bone-facing side of the bone plate.

16. The surgical instrument of claim 9, wherein the barrel has a first barrel use position and a second barrel use position 180° relative to the first barrel use position.

17. The surgical instrument of claim 9, further comprising: a biasing element positioned within the second actuator and engaging a proximal end of the proximal housing, the biasing element configured to bias the proximal housing distally.

18. The surgical instrument of claim 17, wherein actuation of the second actuator includes overcoming a biasing force of the biasing element to cause rotation of the proximal housing.

19. A surgical instrument comprising:
- an elongate body having a proximal housing and a distal housing, the proximal housing configured to rotate relative to the distal housing and the distal housing configured to engage a bone plate;
- a barrel fixed to the proximal housing configured to rotate about the elongate body with rotation of the proximal housing;
- a first actuator engaged with the proximal housing and operably associated with the proximal housing such that the proximal housing rotates relative to the distal housing upon actuation of the first actuator, and
- a second actuator positioned proximal to the first actuator, the second actuator configured to causing locking and unlocking of the distal housing relative to the bone plate.

20. The surgical instrument of claim 19, further comprising a drawbar configured to move proximally or distally within the elongate body upon actuation of the second actuator,
- wherein actuation of the drawbar in the proximal direction causes the distal housing to lock relative to the bone plate; and wherein actuation of the drawbar in the distal direction causes expansion of the distal housing to unlock the distal housing relative to the bone plate.

* * * * *